United States Patent
Ohmori et al.

(10) Patent No.: US 8,153,142 B2
(45) Date of Patent: *Apr. 10, 2012

(54) SKIN TREATMENT COMPOSITION

(75) Inventors: Takashi Ohmori, Yokohama (JP);
Tohru Okamoto, Yokohama (JP);
Hiroyuki Kakoki, Yokohama (JP); Reji Miyahara, Yokohama (JP); Tomiyuki Nanba, Yokohama (JP); Toshihiko Nakane, Yokohama (JP); Yohei Hamano, Yokohama (JP); Eriko Takeoka, Yokohama (JP)

(73) Assignees: Shiseido Co., Ltd., Tokyo (JP); NOF Corporation, Tokyo (JP)

( * ) Notice: Subject to any disclaimer, the term of this patent is extended or adjusted under 35 U.S.C. 154(b) by 312 days.

This patent is subject to a terminal disclaimer.

(21) Appl. No.: 12/461,426

(22) Filed: Aug. 11, 2009

(65) Prior Publication Data

US 2010/0209370 A1      Aug. 19, 2010

Related U.S. Application Data

(62) Division of application No. 10/134,441, filed on Apr. 30, 2002, now Pat. No. 7,625,574.

(30) Foreign Application Priority Data

Sep. 28, 2001 (JP) ................................ 2001-304029
Mar. 27, 2002 (JP) ................................ 2002-89259
Mar. 29, 2002 (JP) ................................ 2002-95092

(51) Int. Cl.
*A61K 9/00* (2006.01)
*A61K 8/02* (2006.01)
*A01N 5/00* (2006.01)
*A61Q 7/00* (2006.01)

(52) U.S. Cl. .................... 424/400; 424/70.11; 424/401; 514/946; 514/947

(58) Field of Classification Search .................. None
See application file for complete search history.

(56) References Cited

U.S. PATENT DOCUMENTS 3,873,696 A      3/1975   Randeri et al.
(Continued)

FOREIGN PATENT DOCUMENTS

EP      0 868 898 A      10/1998
(Continued)

OTHER PUBLICATIONS

Meeuwis et al. (Acta Derm Venereol 2011, 91; 5-11).*
(Continued)

*Primary Examiner* — Ernst Arnold
(74) *Attorney, Agent, or Firm* — Andrews Kurth, LLP; Michael Ye

(57) ABSTRACT

A skin treatment composition of the present invention is an external composition for skin comprising an alkylene oxide derivative expressed by Formula (I):

$$R^1O-[(AO)_m(EO)_n]-R^2 \qquad (I)$$

wherein AO is an oxyalkylene group of $C_3$ or $C_4$; EO is an oxyethylene group; m and n are $1 \leq m \leq 70$ and $1 \leq n \leq 70$ respectively, wherein EO is 20~80% by weight with respect to a total of AO and EO; each of $R^1$ and $R^2$ is a hydrogen or a hydrocarbon group having $C_{1-4}$. The alkylene oxide derivative (I) has a moisturizing effect, a rough skin improving effect, a stickiness improving effect, and a transdermal absorption promoting effect. When a refreshing agent is used together therewith in the composition of the present invention, the refreshing effect lasts for a long time and it is excellent in feeling of use without skin stimulation.

30 Claims, 4 Drawing Sheets

Alkylene oxide derivative

U.S. PATENT DOCUMENTS

| | | | |
|---|---|---|---|
| 4,226,889 A | 10/1980 | Yuhas | |
| 4,301,083 A | 11/1981 | Yoshimura et al. | |
| 4,438,011 A | 3/1984 | Howes | |
| 4,524,062 A | 6/1985 | Laba et al. | |
| 4,596,653 A | 6/1986 | Graham et al. | |
| 4,780,465 A | 10/1988 | Ogata et al. | |
| 5,614,179 A | 3/1997 | Murphy et al. | |
| 5,616,335 A | 4/1997 | Nicolle et al. | |
| 5,696,171 A | 12/1997 | Rupp et al. | |
| 5,709,849 A | 1/1998 | Ito et al. | |
| 5,798,437 A | 8/1998 | Hancock et al. | |
| 5,942,214 A | 8/1999 | Lucas et al. | |
| 6,117,418 A | 9/2000 | Matesevac et al. | |
| 6,284,234 B1 | 9/2001 | Niemiec et al. | |
| 6,544,953 B2 | 4/2003 | Tsuzuki et al. | |
| 6,797,399 B2 | 9/2004 | Weuthen et al. | |
| 2002/0018760 A1 | 2/2002 | Vatter et al. | |

FOREIGN PATENT DOCUMENTS

| | | |
|---|---|---|
| JP | 58-172309 | 10/1983 |
| JP | 01-102013 | 4/1989 |
| JP | 6-100894 | 4/1994 |
| JP | 8-026929 | 1/1996 |
| JP | 08-304536 | 5/1998 |
| JP | 10-167948 | 6/1998 |
| JP | 09-066240 | 9/1998 |
| JP | 09-307490 | 5/1999 |
| JP | 09-348092 | 7/1999 |
| JP | 10-018786 | 8/1999 |
| JP | 2000160191 A | 6/2000 |
| JP | 200 003098 | 1/2001 |
| JP | 2001-089357 | 4/2001 |
| WO | WO 92/19216 | 11/1992 |
| WO | WO 01/13876 | 3/2001 |
| WO | WO 01/77281 | 10/2001 |

OTHER PUBLICATIONS

Cowan-Lincoln Jun./Jul. 2011: 4 pages: [online] retrieved from: http://www.pharmaquality.com/ME2/Audiences/dirmod.asp?sid=325598564E8C4B3EB736C7159241312D&nm=Browse+Articles&type=Publishing&mod=Publications%3A%3AArticle&mid=D3E3C719D8D44216836DCA4F4144BEC4&tier=4&id=BB7F6BA2     BE234DA3A990DDB47A0E0C01&AudID=5648A5C28C97462D1313DB309539B820EF.*

Finnin et al. Journal of Pharmaceutical Sciences, 88(10), 955-958), 1999.*

Gordon et al. (Clinical, Cosmetic and Investigational Dermatology 2011, 4, pp. 101-106).*

Machine Translation of (JP, 11-181689,A) 6-7-199. 11 pages, Jun. 7, 1999.

Persson et al, (Journal of Chromatography 2000, 743, 115-126).

Derwent-Acc-No. 2000-485431 abstracting JP2000160191A, Jun. 13, 2000.

English Translation of Surfactant Industry, Tsinghua Tongfang Optical Disc Co., Ltd., p. 1 (right-column; bracketed), 1995-2005.

* cited by examiner

SKIN TREATMENT COMPOSITION

RELATED APPLICATIONS

This application is a Divisional Application of U.S. patent application Ser. No. 10/134,441, filed on Apr. 30, 2002, now U.S. Pat. No. 7,625,574 which claims the priority of Japanese Patent Application Nos. 2001-304029 filed on Sep. 28, 2001, 2002-89259 filed on Mar. 27, 2002, and 2002-95092 filed on Mar. 29, 2002, all of which are incorporated herein by references.

FIELD OF THE INVENTION

The present invention relates to a skin treatment composition and, in particular, to an external composition for skin comprising an alkylene oxide derivative as an effective ingredient and having a moisturizing effect, a rough skin improving effect, a favorable feeling of use, a transdermal absorption promoting effect, a durability of refreshing effect, and no skin stimulation.

BACKGROUND OF THE INVENTION

In order to retain the healthy skin, moisture retention is essentially, and many external compositions for skin have been developed for the purpose of moisturizing. In addition, as the feeling of use for an external composition for skin, the smoothness and no stickiness are demanded.

Humectants have been intensively studied, an example of a humectant used for many utilities such as a skin lotion and a milky lotion includes glycerin. Glycerin has an effect of improving rough skin in addition to a moisturizing effect.

However, in order to enhance the moisturizing effect and the rough skin improvement effect, an amount of glycerin to be incorporated must be increased and, as a result, there are problems that the composition becomes unstable, the usability is deteriorated and, when applied on skin, it is repelled by sebum, and the compatibility with skin is deteriorated.

As a humectant other than glycerin, polyols such as 1,3-butylene glycol, propylene glycol, polyethylene glycol, sorbitol, xylitol and the like have been known.

These polyols have the better feeling of use, for example, have little sticky feeling as compared with glycerin. However, there are problems that they have lower moisturizing and rough skin improving effects and, like glycerin, when applied on skin, they are repelled by sebum and the compatibility with skin is deteriorated.

On the other hand, in an external composition for skin, a refreshing agent, representatives of which are menthol and camphor, is widely used for imparting a refreshing feeling to skin, alternatively, incorporated for a purpose of improvement in swelling, deteriorated circulation or a mucosal swelling, local resolution, anti-itching, remission or the like.

Menthol and camphor exert the effect by volatilizing from a base of an external composition. There is a problem that, when the concentration thereof is low, the effect does not last and, when the concentration is increased in order to enhance the durability, skin stimulation is too strong to generate a smart feeling and redness.

Recently, there are many products which are applied on skin near eyes or near mouth for the purpose of improving and preventing swelling and bags around eyes, or shaking off sleepiness or improving nasal congestion. Like this, when applied on a comparatively delicate site near a mucosa, since an amount of the refreshing agent to be incorporated is limited, it is difficult to obtain a product having a high durability of the refreshing effect. Of course, in such an external composition for skin, the feeling of use is also a very important factor, and smoothness, moist feeling, no stickiness and the like are required.

SUMMARY OF THE INVENTION

The present invention has been done in view of the problems of the previous art, and an object of the present invention is to provide an external composition for skin which has a moisturizing and rough skin improving effects together with a favorable feeling of use Also, an object of the present invention is to provide an external composition for skin which can retain a refreshing effect for along period of time, has no skin stimulation such as a smart feeling and is excellent in the feeling of use.

In order to attain the aforementioned objects, the present inventors studied intensively and, as a result, it has been found that, by incorporating a particular alkylene oxide derivative, an external composition for skin was obtained which was excellent in feeling of use, especially in smoothness and in no sticky feeling and had moisturizing and rough skin improving effects. In addition, when the alkylene oxide derivative was used together with a humectant such as glycerin, the transdermal absorption of the humectant was promoted, and the moisturizing and rough skin improving effects were remarkably improved synergistically, as well as the stickiness due to the humectant was also improved. Further, the alkylene oxide derivative exerted the transdermal absorption promoting activity to a skin whitening agent such as arbutin. Also, it has been found that, when the alkylene oxide derivative was incorporated together with a refreshing agent, an external composition for skin was obtained which had an improved durability of the refreshing effect, no skin stimulation and an excellent feeling of use, which resulted in completion of the present invention.

Namely, an external composition for skin comprises an alkylene oxide derivative expressed by Formula (I):

$$R^1O-[(AO)_m(EO)_n]-R^2 \qquad (I)$$

wherein AO is an oxyalkylene group having a carbon number of 3 or 4; EO is an oxyethylene group; m and n are average addition numbers of said AO and EO respectively which are $1 \leq m \leq 70$ and $1 \leq n \leq 70$, wherein said EO is 20~80% by weight with respect to a total of said AO and EO and wherein AO and EO may be added each other as being block or random; and each of $R^1$ and $R^2$, which may be identical to or different from each other, is a hydrogen atom or a hydrocarbon group having a carbon number of 1-4, wherein a ratio of the hydrocarbon atom number with respect to the hydrocarbon group number in $R^1$ and $R^2$ is 0.15 or less.

In the present invention, the oxyalkylene group AO and the oxyethylene group EO are preferably added each other in a random form.

In the composition of the present invention, said alkylene oxide derivative (I) is preferably 0.01 to 70% by weight.

A moisturizing agent in accordance with the present invention comprises, as an effective ingredient, said alkylene oxide derivative expressed by Formula (I).

A rough skin improving agent in accordance with the present invention comprises, as an effective ingredient, said alkylene oxide derivative expressed by Formula (I).

A stickiness improving agent in accordance with the present invention comprises, as an effective ingredient, said alkylene oxide derivative expressed by Formula (I).

A transdermal absorption promoting agent in accordance with the present invention comprises, as an effective ingredient, said alkylene oxide derivative expressed by Formula (I).

Also, an external composition for skin of the present invention comprises said alkylene oxide derivative expressed by Formula (I) together with a water-soluble medicament and said alkylene oxide derivative is a transdermal absorption improving agent for said water-soluble medicament.

In the present invention, said water-soluble medicament is preferably a humectant, more preferably, glycerin or xylitol.

Also, In the present invention, said water-soluble medicament is preferably at least one selected from a group of hydroquinone derivatives and ascorbic acid derivatives.

A transdermal absorption controlling agent in accordance with the present invention comprises, as an effective ingredient, said alkylene oxide derivative expressed by Formula (I).

Also, an external composition for skin of the present invention comprises a refreshing agent together with said alkylene oxide derivative expressed by Formula (I). In the composition, said alkylene oxide derivative (I) is preferably 0.1-80% by weight.

In the present invention, said refreshing agent is preferably menthol or camphor.

In the present invention, said refreshing agent is preferably 0.001-20% by weight.

A method for moisturizing human skin of the present invention comprises applying said composition on human skin.

A method for improving human rough skin of the present invention comprises applying said composition on human skin.

A method for improving a stickiness of an external composition for skin of the present invention comprises adding an effective amount of said alkylene oxide derivative expressed by Formula (I) to said composition.

A method for promoting a transdermal absorption of a water-soluble medicament of the present invention comprises: adding an effective amount of said alkylene oxide derivative expressed by Formula (I) to an external composition for skin containing said water-soluble medicament; and applying said composition on human skin.

BEST MODE FOR CARRYING OUT THE INVENTION

Figure 1:
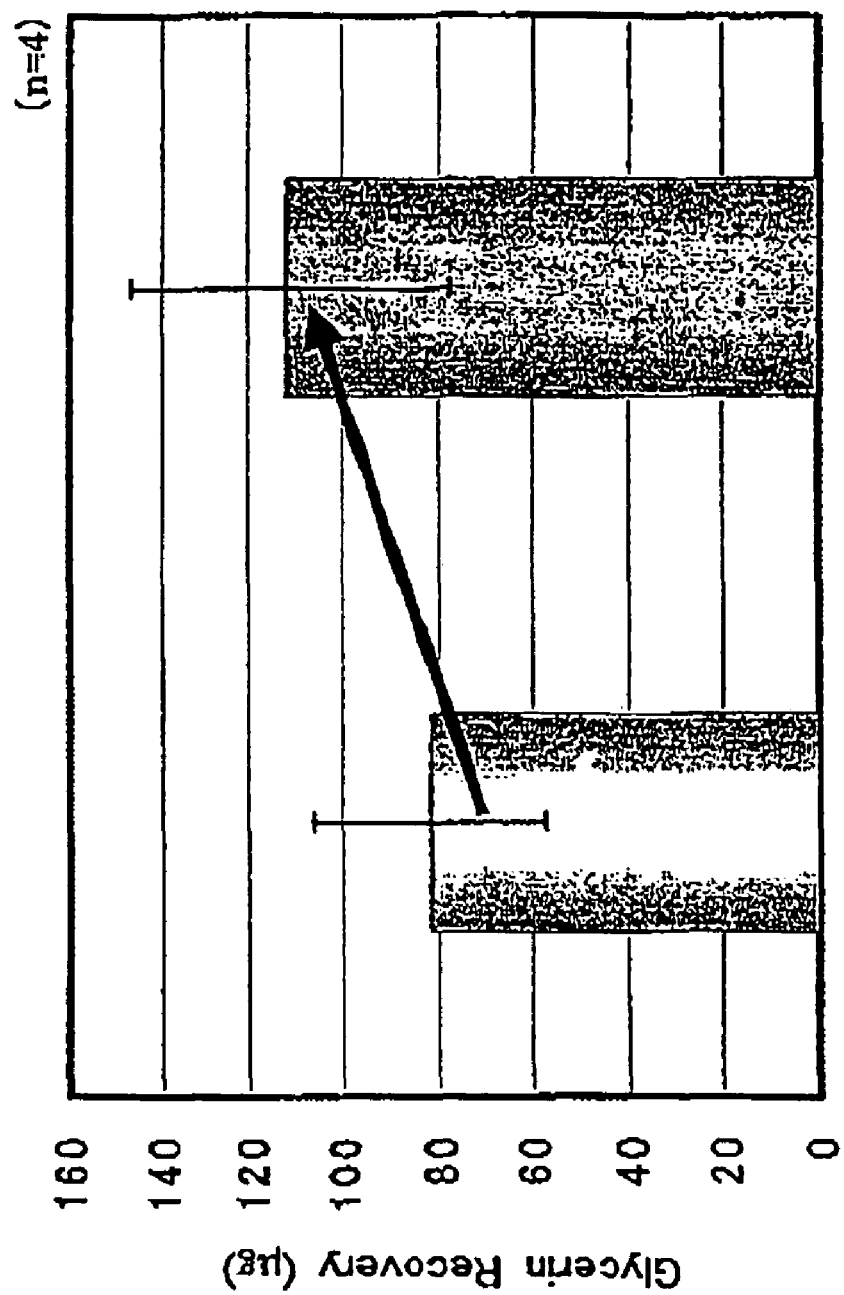
FIG. 1 shows a transdermal absorption promoting effect of an alkylene oxide derivative in accordance with the present invention to glycerin.

In an alkylene oxide derivative represented by Formula (I) which is characteristic in the present invention, AO is an oxyalkylene group having a carbon number of 3-4, such as an oxypropylene group, an oxybutylene group, an oxyisobutylene group, an oxytrimethylene group and an oxytetramethylene group. Preferable examples include an oxypropylene group and an oxybutylene group.

"m" is an average addition mole number of the oxyalkylene group having a carbon number of 3-4, being $1 \leq m \leq 70$, preferably $2 \leq m \leq 20$. "n" is an average addition mole number of the oxyethylene group, being $1 \leq n \leq 70$, preferably $2 \leq n \leq 20$. When the average addition mole number m or n is 0, a moist feeling may be deteriorated or the effect of the present invention may not be obtained sufficiently whereas when the number exceeds 70, a sticky feeling may be generated and a smooth feeling can not be obtained sufficiently.

In addition, it is preferable that the oxyethylene group is 20-80% by weight with respect to a total of the oxyalkylene group having a carbon number of 3-4 and the oxyethylene group. When the oxyethylene group is less than 20% by weight, there is a tendency that the moist feeling is inferior or the effect of the present invention is not demonstrated sufficiently, whereas when it exceeds 80% by weight, there is a tendency that the smooth feeling is inferior.

An addition order of ethylene oxide and alkylene oxide having a carbon number of 3-4 is not particularly limited. Also, the oxyethylene group EO and the oxyalkylene group AO may be added in a block- or random-form. The block-form includes not only two-stepwise block and but also three or more-stepwise block. A preferable example includes random addition.

Each of $R^1$ and $R^2$ is a hydrocarbon group having a carbon number of 1-4 or a hydrogen atom, and examples of the hydrocarbon groups include methyl, ethyl, n-propyl, isopropyl, n-butyl, sec-butyl and tert-butyl groups. Preferable examples include methyl and ethyl group. In the case of the hydrocarbon group having a carbon number of 5 or more, the hydrophilic property is lowered and there is a tendency that the moist feeling or the effect of the present invention is, deteriorated. $R^1$ and $R^2$ may be the same or different from each other.

Only one kind of $R^1$ and $R^2$ may be used. Alternatively, in each of $R^1$ and $R^2$, a hydrocarbon group having a carbon number of 1-4 and a hydrogen atom may be present together, or different kind of hydrocarbon groups having a carbon number of 1-4 may be present together. Regarding the hydrocarbon groups of $R^1$ and $R^2$, however, Y/X which is a ratio of the number of hydrogen atom (Y) with respect to the number of hydrocarbon group (X) is 0.15 or less, preferably 0.06 or less. When the ratio of Y/X exceeds 0.15, a sticky feeling is generated.

The alkylene oxide derivative of the present invention can be prepared by a known method. For example, ethylene oxide and alkylene oxide having a carbon number of 3-4 are additionally polymerized with a compound having a hydroxyl group, and then an alkyl halide is reacted therewith in the presence of a basic catalyst to perform etherification, to give an alkylene oxide derivative.

The alkylene oxide derivative of the present invention can exert a moisturizing effect and a rough skin improving effect when incorporated into an external composition for skin. In addition, when a conventional humectant such as glycerin is incorporated thereto, the alkylene oxide derivative can suppress the stickiness due to the humectant. Examples of humectants which can be used together with the alkylene oxide derivative include polyethylene glycol, propylene glycol, glycerin, 1,3-butylene glycol, xylitol, sorbitol, maltitol, chondroitin sulfate, hyaluronic acid, mucoitin sulfate, charonin acid, atello-collagen, cholesteryl-12-hydroxystearate, sodium lactate, bile salt, dl-pyrrolidone carboxylate, short chain soluble collagen, diglycerin(EO)PO adduct, the sixteen night rose extract, yarrow extract, melirote extract and the like.

The alkylene oxide derivative (I) of the present invention also has an action of promoting the keratin permeability of a conventional humectant. Therefore, when the alkylene oxide derivative (I) and the humectant are used together in an external composition for skin, an extremely high moisturizing effect and rough skin improving effect can be obtained synergistically. Examples of such humectant include those described above, and glycerin and xylitol are particularly preferable.

An amount of the humectant to be incorporated, which is not particularly limited to, is preferably 0.001-20.00% by weight, more preferably 0.1-10.0% by weight based on the whole of an external composition for skin.

The alkylene oxide derivative (I) of the present invention has the action of promoting the keratin permeability also on a hydrophilic medicament other than a humectant, for example, a skin whitening agent such as arbutin.

For the effects mentioned above, the alkylene oxide derivative to be incorporated into an external composition for skin, which is not particularly limited to, is usually around 0.01-70% by weight, preferably around 0.5-40% by weight. When it is less than 0.01% by weight, the effect may not be sufficiently demonstrated, whereas when it exceeds 70% by weight, a sticky feeling may be generated after use.

A refreshing agent used in the present invention means a agent which is volatilized from a base applied on skin to impart a refreshing feeling to skin and to exert an effect of improving swelling and bags, a resolution effect, a remission effect, an anti-itching effect and the like (collectively referred to as refreshing effect in the present invention) and which can be incorporated in an external composition for skin (mainly terpenes or its similar ingredients). Although lower alcohols such as ethanol and volatile solvents such as volatile oils can impart a refreshing feeling, these are not usually contained in a refreshing agent (of course, there is no problem that they are used together with a refreshing agent).

As a preferable refreshing agent, there are menthol and camphor, which may be natural or synthetic. Examples of menthol include 1-menthol, dl-menthol and menthe oil, and examples of camphor include d-camphor and dl-camphor. In the present invention, two or more kinds of refreshing agents may be used in combination.

An amount of the refreshing agent in the external composition for skin of the present invention, which is different depending on the purpose of the composition, is usually 0.001-20% by weight, preferably 0.01-10% by weight. The refreshing agent can be incorporated into the external composition for skin by an usual method. For example, any methods such as solubilizing, suspending or emulsifying method can be used.

It is preferable that the refreshing agent is dissolved in the external composition for skin in view of usability. Therefore, the base of the external composition for skin to be used in the present invention preferably contains a suitable solvent for the refreshing agent, and examples thereof include lower alcohol such as ethanol, oils and the like.

The alkylene oxide derivative (I) of the present invention improves the durability of the refreshing effect and lowers the skin stimulation such as a smart feeling due to the refreshing agent. Although the mechanism is not clear, it can be considered that when the alkylene oxide derivative (I) exists in the external composition for skin, the refreshing agent evaporates little by little, whereby a mild refreshing feeling can last for a long time.

When the alkylene oxide derivative is used together with a refreshing agent, an amount of the derivative, which is not particularly limited to, is usually around 0.1-80.0% by weight, preferably around 5.0-40.0% by weight based on the whole of the external composition for skin. When it is too less, the effect of the present invention may not be demonstrated sufficiently, whereas when it is excess, a sticky feeling may be generated after use.

The external composition for skin of the present invention is prepared by incorporating the aforementioned essential ingredients into a known base for an external composition for skin. The external composition for skin of the present invention can be prepared by appropriately incorporating, in addition to the aforementioned essential ingredients, ingredients normally used in a cosmetic or a medical external composition for skin, according to the conventional method depending upon desired forms. Examples of ingredients normally used include powders, liquid fat or oils, solid fat or oils, waxes, hydrocarbons, higher fatty acids, higher alcohols, esters, silicones, anionic surfactants, cationic surfactants, amphoteric surfactants, nonionic surfactants, water-soluble polymers, thickeners, film-forming agents, ultraviolet absorbing agents, metal ion sequestering agents, lower alcohols, multivalent alcohols, sugars, amino acids, organic amines, polymer emulsions, pH adjusting agents, skin nutrients, vitamins, antioxidants, antioxidant aids, perfumes, water and the like. Specific examples thereof will be listed below. The external composition for skin of the present invention can be prepared by incorporating aforementioned essential ingredients and one or more kinds of ingredients described below.

Examples of powders include inorganic powders (e.g., talc, kaolin, mica, sericite, muscovite, phlogopite, synthetic mica, red mica, biotite, vermiculite, magnesium carbonate, calcium carbonate, aluminum silicate, valium silicate, calcium silicate, magnesium silicate, strontium silicate, tungsten acid metal salt, magnesium, silica, zeolite, barium sulfate, calcinated calcium sulfate (calcined gypsum), calcium phosphate, fluorine apatite, hydroxyapatite, ceramic powder, metal soap (e.g., zinc myristate, calcium palmitate, aluminium stearate), boron nitride and the like); organic powders (e.g., polyamide resin powder (nylon powder), polyethylene powder, methyl polymethacrylate powder, polystyrene powder, resin powder of copolymer of styrene and acrylic acid, benzoguanamine resin powder, polyethylene tetrafluoride powder, cellulose powder and the like); inorganic white pigments (e.g., titanium dioxide, zinc oxide and the like); inorganic red series pigments (e.g., iron oxide (red iron oxide), iron titanate and the like); inorganic brown series pigments (e.g., γ-iron oxide and the like); inorganic yellow series pigments (e.g., yellow iron oxide, loess and the like); inorganic black series pigments (e.g., black iron oxide, lower titanium oxide and the like); inorganic purple series pigments (e.g., mangoviolet, cobaltviolet and the like); inorganic green series pigments (e.g., chromium oxide, chromium hydroxide, cobalt titanate and the like); inorganic blue series pigments (e.g., ultramarine, Prussian blue and the like); pearl pigments (e.g., titanium oxide-coated mica, titanium oxide-coated bismuth oxychloride, titanium oxide-coated talc, colored titanium oxide-coated mica, bismuth oxychloride, fish scale foil and the like); metal powder pigments (e.g., aluminum powder, copper powder and the like); organic pigments such as zirconium, barium or aluminum lake and the like (e.g., organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404, Red No. 3, Red No. 104, Red No. 106, Red No.

227, Red No. 230, Red No. 401, Red No. 505, Orange No. 205, Yellow No. 4, Yellow No. 5, Yellow No. 202, Yellow No. 203, Green No. 3, and Blue No. 1 and the like); natural colors (e.g., chlorophyll, β-carotene and the like).

Examples of liquid fat or oils include avocado oil, camellia oil, turtle oil, macadamia nut oil, corn oil, mink oil, olive oil, rapeseed oil, yolk oil, sesame oil, persicary oil, wheet germ oil, sasanqua oil, castor oil, linseed oil, safflower oil, cottonseed oil, perilla oil, soybean oil, peanut oil, tea seed oil, kaya seed oil, rice bran oil, Chinese paulownia oil, Japanese paulownia oil, jojoba oil, germ oil, triglycerides and the like.

Examples of solid fat or oils include cacao butter, coconut oil, horse fat, hydrogenated coconut oil, palm oil, beef tallow, mutton tallow, hardened beef tallow, palm kernel oil, lard, beef bone fat, Japan wax kernel oil, hardened oil, beef foot fat, Japan wax, hydrogenated castor oil and the like.

Examples of waxes include beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl, hexyl laurate, reduced lanolin, jojoba wax, hardened lanolin, shellac wax, POE lanolin alcohol ether, POE lanolin alcohol acetate, POE cholesterol ether, lanolin fatty acid polyethylene glycol, POE hydrogenated lanolin alcohol ether and the like.

Examples of the hydrocarbon oil include liquid paraffin, ozokerite, squalane, pristane, paraffin, ceresin, squalene, vaseline, microcrystalline wax and the like.

Examples of the higher fatty acid include lauric acid, myristic acid, palmitic acid, stearic acid, behenic acid, oleic acid, undecylenic acid, tallic acid, isostearic acid, linoleic acid, linolenic acid, eicosapentaenoic acid (EPA), docosahexaenoic acid (DHA) and the like.

Examples of the higher alcohol include straight alcohols (e.g., lauryl alcohol, cetyl alcohol, stearyl alcohol, behenyl alcohol, myristyl alcohol, oleyl alcohol, cetostearyl alcohol and the like); branched alcohols (e.g., monostearylglycerin ether (batyl alcohol), 2-decyltetradecinol, lanolin alcohol, cholesterol, phytosterol, hexyldodecanol, isostearyl alcohol, octyldodecanol and the like) and the like.

Examples of the synthetic ester oil include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, di-2-ethylhexanoic acid ethylene glycol, dipentaerythritol fatty acid ester, monoisostearic acid N-alkyl glycol, dicapric acid neopentyl glycol, diisostearyl malate, di-2-heptylundecanoic acid glycerin, tri-2-ethylhexanoic acid trimethylolpropane, triisostearic acid trimethylolpropane, tetra-2-ethylhexanoic acid pentaerythritol, tri-2-ethylhexanoic acid glycerin, trioctanoic acid glycerin, triisopalmitic acid glycerin, triisostearic acid trimethylolpropane, cetyl 2-ethylhexanoate, 2-ethylhexyl palmitate, trimyristic acid glycerin, tri-2-heptylundecanoic acid glyceride, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate and the like.

Examples of the silicone oil include chain polysiloxane (e.g., dimethylpolysiloxane, methylphenylpolysiloxane, diphenylpolysiloxane and the like); cyclic polysiloxane (e.g., octamethylcyclotetrasiloxane, decamethylcyclopentasiloxane, dodecarmethylcyclohexasiloxane and the like), silicone resins having a three dimensional network structure, silicone rubbers, various modified polysiloxans (amino-modified polysiloxane, polyether-modified polysiloxane, alkyl-modified polysiloxane, fluorine-modified polysiloxane and the like) and the like.

Examples of the anionic surfactant include fatty acid soaps (e.g., sodium laurate, sodium palmitate and the like); higher alkyl sulfates (e.g., sodium laurylsulfate, potassium lauryl sulfate and the like); alkyl ether sulfates (e.g., triethanolamine POE-lauryl sulfate, sodium POE lauryl sulfate and the like); N-acylsarcosinic acids(e.g., sodium lauroylsarcosinate and the like); higher fatty acid amide sulfates (e.g., sodium N-rnyristoyl-N-methyltaurate, sodium cocoyl methyltaurate, sodium lauroyl methyltaurate and the like); phosphates (sodium POE oleyl ether phosphate, POE-stearyl ether phosphoric acid and the like); sulfosuccinates (e.g., sodium di-2-ethylhexylsulfosuccinate, sodium monolauroyl monoethanolamide polyoxyethylenesulfosuccinate, sodium lauryl polypropyleneglycol sulfosuccinate and the like); alkylbenzenesulfonates (e.g., sodium linear dodecylbenzene sulfonate, triethanolamine linear dodecylbenzenesulfonate, linear dodecylbenzenesulfonic acid and the like); higher fatty acid ester sulfates (e.g., sodium hydrogenated cocoglyceride sulfate and the like); N-acylglutamates (e.g., monosodium N-lauroylglutamate, disodium N-stearoylglutamate, monosodium N-myristoyl-L-glutamate and the like); sulfated oils (e.g., turkey red oil and the like); POE alkyl ether carboxylic acids; POE alkyl allyl ether carboxylates; α-olefinsulfonates; higher fatty acid ester sulfonates; secondary alcohol sulfates; higher fatty acid alkylolamide sulfate; sodium lauroyl monoethanolamide succinate; ditriethanolamine N-palmitoylaspartate; sodium caseinate and the like.

Examples of the cationic surfactant include alkyl trimethyl ammonium salts (e.g., stearyl trimethyl ammonium chloride, lauryl trimethyl ammonium chloride and the like); alkyl pyridinium salts (e.g., cetylpyridinium chloride and the like); distearyl dimethyl ammonium chloride dialkyl dimethyl ammonium salt; poly(N,N'-dimethyl-3,5-methylenepiperidinium)chloride; alkyl quaternary ammonium salts; alkyl dimethyl benzyl ammonium salts; alkylisoquinolinium salts; dialkylmorphonium salts; POE alkylamines; alkylamine salts; polyamine fatty acid derivatives; amyl alcohol fatty acid derivatives; benzalkonium chloride; benzetonium chloride and the like:

Examples of the amphoteric surfactant include imidazoline series amphoteric surfactants (e.g., 2-undecyl-N,N,N-(hydroxyethylcarboxymethyl)-2-imidazoline sodium, 2-cocoyl-2-imidazolinium hydroxide-1-carboxyethyloxy disodium salt and the like); betaine series surfactants (e.g., 2-heptadecyl-N-carboxymethyl-N-hydroxyethylimidazolinium betaine, lauryldimethylaminoacetic acid betaine, alkylbetaine, amidebetaine, sulfobetaine and the like) and the like.

Examples of the lipophilic nonionic surfactant include sorbitan fatty acid esters (e.g., sorbitan monooleate, sorbitan monoisostearate, sorbitan monolaurate, sorbitan monopalmitate, sorbitan monostearate, sorbitan sesquioleate, sorbitan trioleate, penta-2-ethylhexylic acid diglycerol sorbitan, tetra-2-ethylhexylic acid diglycerol sorbitan and the like); glycerin polyglycerin fatty acids (e.g., mono-cottonseed oil fatty acid glycerin, monoerucic acid glycerin, sesquioleic acid glycerin, monostearic acid glycerin,α,α'-oleic acid pyroglutamic acid glycerin, monostearic acid glycerin malic acid and the like); propylene glycol fatty acid esters (e.g., monostearic acid propylene glycol and the like); hydrogenated castor oil derivatives; glycerin alkyl ethers and the like.

Examples of the hydrophilic nonionic surfactant include POE-sorbitan fatty acid esters (e.g., POE-sorbitan monooleate, POE-sorbitan monostearate, POE-sorbitan monooleate, POE-sorbitan tetraoleate and the like); POE-sorbit fatty acid esters (e.g., POE-sorbit monolaurate, POE-sorbit monooleate, POE-sorbit pentaoleate, POE-sorbit monostearate and the like); POE-glycerin fatty acid esters (e.g., POE-monooleate and the like such as POE-glyceryl monostearate, POE-glyceryl monoisostearate, and POE-glyceryl triisostearate); POE-fatty acid esters (e.g., POE-distearate, POE-monodioleate, ethylene glycol distearate and the like); POE-alkyl ethers(e.g., POE-lauryl ether, POE-oleyl ether, POE-stearyl ether, POE-behenyl ether, POE-2-octyldodecyl ether, POE-cholestanol ether and the like); Pluronic type surfactants (e.g., Pluronic and the like); POE•POP-alkyl ethers (e.g., POE•POP-cetyl ether, POE•POP-2-decyltetradecyl ether, POE•POP-monobutyl ether, POE•POP-hydrogenated lanolin, POE•POP-glyceryl ether and the like); fused tetraPOE•tetraPOP-ethylenediamines (e.g., Tetronic and the like); POE-castor oil hydrogenated castor oil derivatives (e.g., POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, POE-hydrogenated castor oil maleate and the like); POE-beeswax•lanolin derivatives (e.g., POE-sorbit beeswax and the like); alkanolamides (e.g., coconut oil fatty acid diethanolamide, lauric acid monoethanolamide, fatty acid isopropanolamide and the like); POE-propylene glycol fatty acid esters; POE-alkylamines; POE-fatty acid amides; sucrose fatty acid esters; alkylethoxydimethylamine oxides; trioleylphosphoric acid and the like.

Examples of the natural water-soluble polymer include plant series polymers (e.g., gum arabic, tragacanth gum, galactan, guar gum, carob gum, karaya gum, carrageenan, pectin, agar, quinceseed (Cydonia oblonga), Alga colloid (brown alga extract), starch (rice, corn, potato, wheat), and glycyrrhizic acid); microorganizm series polymers (e.g., xanthan gum, dextran, succinoglucan, pullulan and the like); animal series polymers (e.g., collagen, casein, albumin, gelatin and the like) and the like.

Examples of the semi-synthetic water-soluble polymer include starch series polymers (e.g., carboxymethylstarch, methylhydroxypropylstarch and the like); cellulose series polymers (methylcellulose, ethylcellulose, methylhydroxypropylcellulose, hydroxyethylcellulose, cellulose sodium sulfate, hydroxypropylcellulose, carboxymethylcellulose, sodium carboxymethylcellulose, crystalline cellulose, cellulose powder and the like); alginic acid series polymers (e.g., sodium alginate, alginic acid propylane glycol ester and the like) and the like.

Examples of the synthetic water-soluble polymer include vinyl series polymers (e.g., polyvinyl alcohol, polyvinyl methyl ether, polyvinyl pyrrolidone, carboxyvinyl polymer and the like); polyoxyethylene series polymers (e.g., polyoxyethylene polyoxypropylene copolymer of polyethylene glycol 20,000, 40,000, 60,000 and the like); acrylic series polymers (e.g., sodium polyacrylate, polyethyl acrylate, polyacrylamide and the like); polyethyleneimine; cationic polymer and the like.

Examples of the thickener include gum arabic, carrageenan, karaya gum, tragacanth gum, carob gum, quinceseed (Cydonia oblonga), caseine, dextrin, gelatin, sodium pectinate, sodium alginate, methylcellulose, ethylcellulose, CMC, hydroxyethylcellulose, hydroxypropylcellulose, PVA, PVM, PVP, sodium polyacrylate, carboxyvinyl polymer, locust bean gum, guar gum, tamarind gum, dialkyldimethylammonium sulfate cellulose, xanthan gum, aluminium magnesium silicate, bentonite, hectorite, AlMg silicate (Veegum), laponite, anhydrous silicic acid and the like.

Examples of the ultraviolet absorbing agent include benzoic acid series ultraviolet absorbing agents (e.g., paraaminobenzoic acid (hereinafter, abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester and the like); anthranilic acid series ultraviolet absorbing agents (e.g., homomenthyl-N-acetyl anthranilate and the like); salicylic acid series ultraviolet absorbing agents (e.g., amyl salicylate, menthyl salicylate, homomenthyl salicylate, octyl salicylate, phenyl salicylate, benzyl salicylate, p-isopropanol phenyl salicylate and the like); sinnamic acid series ultraviolet absorbing agents (e.g., octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-diparamethoxy cinnamate and the like); benzophenone series ultraviolet absorbing agents (e.g., 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone and the like); 3-(4'-methylbenzylidene)-d,l-camphor, 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenylbenzotriazole; dibenzaladine; dianisoylmethane; 4-methoxy-4'-t-butyldibenzoylmethane; 5-(3,3-dimethyl-2-norbornylidene)-3-pentane-2-one and the like.

Examples of the sequestering agent include 1-hydroxyethane-1,1-diphosphonic acid, tetrasodium 1-hydroxyethane-1,1-diphosphonate, disodium edetate, trisodiurn edetate, tetrasodium edetate, sodium citrate, sodium polyphosphate, sodium methaphosphate, gluconic acid, phosphoric acid, citric acid, ascorbic acid, succinic acid, edetic acid, trisodium ethylenediaminehydroxyethyltriacetate and the like.

Examples of the lower alcohol include ethanol, propanol, isopropanol, isobutyl alcohol, t-butyl alcohol and the like:

Examples of the polyol include diols (e.g., ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol and the like); triols (e.g., glycerin trimethylolpropane and the like); tetraols (e.g., pentaerythritol such as 1,2,6-hexanetriol and the like); pentaols (e.g., xylitol and the like); hexaols (sorbitol, mannitol and the like); polyol polymers (e.g., diethylene glycol, dipropylene glycol, triethylene glycol, polypropylene glycol, tetraethylene glycol, diglycerin, polyethylene glycol, triglycerin, tetraglycerin, polyglycerin and the like); diol alkyl ethers (e.g., ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether and the like); diol alkyl ethers (e.g., diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether and the like); diol ether ester (e.g., ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate and the like); glycerin monoalkyl ether (e.g., xyl alcohol, selachyl alcohol, batyl alcohol and the like); suger alcohol (e.g., sorbitol, maltitol, maltotriose, mannitol, sucrose, erythritol, glucose, fructose, starch-degraded suger, maltose, xylulose, starch-degraded suger reduced alcohol and the like); glysolid; tetrahydrofurfuryl alcohol; POE-tetrahydrofurfuryl alcohol; POP-butyl ether; POP•POE-butyl ether; tripolyoxypropylene glycerin ether; POP-glycerin ether; POP-glycerin ether phosphoric acid; POP•POE-pentaerythritol ether, polyglycerin and the like.

Examples of the monosaccharide include trioses (e.g., D-glycerylaldehyde, dihydroxyacetone and the like); tetroses (e.g., D-erythrose, D-erythrulose, D-threose, erythritol and the like); pentoses (e.g., L-arabinose, D-xylose, L-lyxose, D-arabinose, D-ribose, D-ribulose, D-xylulose, L-xylulose and the like); hexoses (e.g., D-glucose, D-talose, D-psicose, D-galactose, D-fructose, L-galactose, L-mannose, D-tagatose and the like); heptoses (e.g., aldoheptose, heprose and the like); octoses (e.g., octulose and the like); deoxysugars (e.g., 2-deoxy-D-ribose, 6-deoxy-L-galactose, 6-deoxy-L-mannose and the like); aminosuger (e.g., D-glucosamine, D-galactosamine, sialic acid, aminouronic acid, muramic acid and the like); uronic acids (e.g., D-glucronic acid, D-mannuronic acid, L-guluronic acid, D-galacturonic acid, L-iduronic acid and the like) and the like.

Examples of the oligosaccharide include sucrose, guntianose, umbelliforose, lactose, planteose, isoliqunoses, α,α-trehalose, raffinose, liqunoses, umbilisine, stachyose belbascoses and the like.

Examples of the polysaccharide include cellulose, quinceseed, chondroitin sulfate, starch, galactan, dermatan sulfate, glycogen, gum arabic, heparan sulfate, hyaluronic acid, tragacanth gum, keratan sulfate, chondroitin, xanthan gum, mucoitin sulfate, guar gum, dextran, kerato sulfate, locust bean gum, succinoglucan, charonic acid and the like.

Examples of the amino acid include neutral amino acids (e.g., threonine, cysteine and the like); basic amino acids (e.g., hydroxylysine and the like) and the like. In addition, examples of the amino acid derivative include sodium acylsarcosinate (sodium lauroylsarcosinate), acylglutamiate, sodium acyl β-alanine, glutathione, pyrrolidinecarboxylic acid and the like.

Examples of the organic amine include monoethanolamine, diethanolamine, triethanolamine, morpholine, triisopropanolamine, 2-amino-2-methyl-1,3-propanediol, 2-amino-2-methyl-1-propanol and the like.

Examples of the polymer emulsion include acrylic resin emulsion, ethyl polyacrylate emulsion, acrylic resin solution, alkyl polyacrylate emulsion, polyvinyl acetate resin emulsion, natural rubber latex and the like.

Examples of the pH adjusting agent include buffers such as lactic acid-sodium lactate, citric acid-sodium citrate, succinic acid-sodium succinate and the like.

Examples of the vitamins include vitamins A, B1, B2, B6, C and E and derivatives thereof, pantothenic acid and derivatives thereof, biotinic acid and the like.

Examples of the antioxidant include tocopherols, dibutylhydroxytoluene, butylhydroxyanisole, gallic acid esters and the like.

Examples of the antioxidant aid include phosphoric acid, citric acid, ascorbic acid, maleic acid, malonic acid, succinic acid, fumaric acid, cephalin, hexamethaphosphate, phytic acid, ethylenediaminetetraacetic acid and the like.

Examples of the other ingredients which can be incorporated include preservatives (e.g., ethylparaben, butylparaben and the like); anti-inflammatory agents (e.g., glycyrrhizic acid derivatives, glycyrrhetic acid derivatives, salicylic acid derivatives, hinokitiol, zinc oxide, allantoin and the like); skin whitening agents (e.g., saxifragaceae extract, arbutin, tranexamic acid, ascorbyl glucoside, magnesium ascorbyl phosphate, ethyl ascorbic acid and the like); various extracts (e.g., plantago, gold thread, bluish purple, peony, Japanese green gentian, birch, sage, loquat, carrot, aloe, mallow, iris, grape, yokinin, snake gourd, lily, saffron, senkyu, shokyu, Saint-John's-wort, ononis, garlic, Guine pepper, dried orange peel, Angelica, alga and the like); activating agents (e.g., royal jelly, photosensitive element, cholesterol derivative and the like); circulation promoting agents (e.g., nonylic acid vanillylamide, nicotinic acid benzyl ester, nicotinic acid β-butoxyethyl ester, capsaicin, zyngerone, cantharidis tincture, ichthammol, tannic acid, α-borneol, nicotinic acid tocopherol, inositol hexanicotinate, cyclandelate, cinnarizine, tolazoline, acetylcholine, verapamil, cepharanthine, γ-oryzanol and the like); antiseborrheic agents (e.g., sulfur, thianthol and the like); anti-inflammatory agents (e.g., thiotaurine, hypotaurine and the like).

Pharmaceutical forms of the external composition for skin of the present invention can be set freely, and any forms such as solution, solubilizing liquid, emulsion, powder dispersion, water-oil bilayer form, water-oil-powder trilayer form, gel, mist, spray, mousse, roll-on and the like can be used. It can be a sheet such as nonwoven fabric wet or coated with the composition. Product forms of the external composition for skin of the present invention can also be set freely, for example, facial cosmetics such as skin lotion, milky lotion, cream, and pack; makeup cosmetics such as foundation, lipstick and eyeshadow; body cosmetics; fragrance cosmetics; skin cleansing cosmetics such as makeup remover and body shampoo; hair cosmetics such as hair liquid, hair tonic, hair conditioner, shampoo, rinse and hair-growth preparation; ointment and the like.

EXAMPLES

In the following, Examples of the present invention will be explained. First, evaluation methods are shown below.
(i) Conductance Measuring Test
Using forearms of 10 panelists, the skin conductance was measured before application and for 30 minutes, 60 minutes and 120 minutes after application, and the moisturizing effect was evaluated from a change rate thereof. The change rate of the skin conductance is calculated by the following equation (II):

Conductance change rate=(conductance before application)/(conductance after application).

The change rate can be used for study of the influences on a water-absorbing property and a moisture retaining ability of a keratin layer. When this change rate is small, there is increase in the moisture in a keratin layer, thus, it can be evaluated that the moisturizing effect is high.

The evaluation criteria of conductance measuring test is as follows:

⊚: The average of conductance change rate of 10 panelists is not less than 0 and less than 0.1
◯: The average of conductance change rate of 10 panelists is not less than 0.1 and less than 0.2
Δ: The average of conductance change rate of 10 panelists is not less than 0.2 and less than 0.5
X: The average of conductance change rate of 10 panelists is not less than 0.5

(ii) Evaluation No.(1): Smoothness of Skin

Practical test on smoothness of skin during use and after use was performed by using 10 special panelists. The evaluation criteria is as follows:

⊚: or more special panelists recognized that the skin was smooth during use and after use.
◯: Not less than 6 and less than 8 special panelists recognized that the skin was smooth during use and after use.
Δ: Not less than 3 and less than 6 special panelists recognized that the skin was smooth during use and after use.
X: Less than 3 special panelists recognized that the skin was smooth during use and after use.

(iii) Evaluation No.(2): No-stickiness on Skin

Practical test on absence of stickiness on the skin during use and after use was performed by using 10 special panelists. The evaluation criteria is as follows:

⊚: Not less than 8 special panelists recognized that there was no stickiness on skin during use and after use.
◯: Not less than 6 and less than 8 special panelists recognized that there was no stickiness on skin during use and after use.
Δ: Not less than 3 and less than 6 special panelists recognized that there was no stickiness on skin during use and after use.
X: Less than 3 special panelists recognized that there was no stickiness on skin during use and after use.

(iv) Evaluation No.(3): Moisturizing Effect Feeling

Practical test on the presence or absence of the moisturizing effect feeling for 120 minutes after use was performed by using 10 special panelists. The evaluation criteria is as follows:

⊚: Not less than 8 special panelists recognized that there was the moisturizing effect feeling.
◯: Not less than 6 and less than 8 special panelists recognized that there was the moisturizing effect feeling.
Δ: Not less than 3 and less than 6 special panelists recognized that there was the moisturizing effect feeling.
X: Less than 3 special panelists recognized that there was the moisturizing effect feeling.

(v) Evaluation No.(4): Rough Skin Improving Effect Test

A rough skin improving effect test was performed by using 10 panelists having rough skin on cheek. According to a test schedule, different skin lotions were applied on left and right cheeks for 1 week, and the effect was determined on the next day after the last day of the test period. The evaluation criteria is as follows:

⊚: Not less than 8 panelists recognized that the rough skin was improved.
◯: Not less than 6 and less than 8 panelists recognized that the rough skin was improved.
Δ: Not less than 3 and less than 6 panelists recognized that the rough skin was improved.
X: Less than 3 panelists recognized that the rough skin was improved.

(iv) Evaluation No.(5): Skin Stimulation Test A

Occluding patch was performed on medial parts of brachiums of 10 panelists for 24 hours and, thereafter, an average was calculated based on the following criteria:

0: No abnormality is perceived.
1: Slight redness is perceived.
2: Redness is perceived.
3: Redness and papula are perceived.

The evaluation criteria of skin stimulation test A is as follows:

⊚: The average of 10 panelists is not less than 0 and less than 0.1
◯: The average of 10 panelists is not less than 0.1 and less than 0.15
Δ: The average of 10 panelists is not less than 0.15 and less than 0.2
X: The average of 10 panelists is not less than 0.2

(vii) Evaluation No.(6): Compatibility with Skin

A compatibility with skin during use was evaluated by 10 special panelists.

The evaluation criteria is as follows:

⊚: Not less than 8 special panelists recognized that the compatibility with skin during use was good.
◯: Not less than 6 and less than 8 special panelists recognized that the compatibility with skin during use was good.
Δ: Not less than 3 and less than 6 special panelists recognized that the compatibility with skin during use was good.
X: Less than 3 special panelists recognized that the compatibility with skin during use was good.

(viii) Evaluation No.(7): Skin Stimulation Test B

A smart feeling when a sample applied on medial parts of brachiums of 10 panelists was graded based on the following criteria and, thereafter, an average was calculated:

0: No smart feeling is perceived.
1: Slight smart feeling or redness is perceived.
2: Smart feeling or redness is perceived.
3: Smart feeling and redness are perceived.

The evaluation criteria of skin stimulation test B is as follows:

⊚: The average of 10 panelists is not less than 0 and less than 0.1
◯: The average of 10 panelists is not less than 0.1 and less than 0.15
Δ: The average of 10 panelists is not less than 0.15 and less than 0.2
X: The average of 10 panelists is not less than 0.2

(ix) Evaluation No.(8): Refreshing Effect Durability

A presence or absence of refreshing feeling for 120 minutes after use was evaluated by 10 special panelists. The evaluation criteria is as follows:

⊚: Not less than 8 special panelists recognized that there was refreshing feeling durability.
◯: Not less than 6 and less than 8 special panelists recognized that there was refreshing feeling durability.
Δ: Not less than 3 and less than 6 special panelists recognized that there was refreshing feeling durability.
X: Less than 3 special panelists recognized that there was refreshing feeling durability.

Next, a synthetic method of an alkylene oxide derivative of the present invention will be shown. In the present invention, EO denotes an oxyethylene group, PO denotes an oxypropylene group, and [(EO)/(PO)] denotes a random bond. Each alkylene oxide derivative used in the present invention was prepared according to the following Synthesis Examples.

Synthesis Example 1

Synthesis of Random Polymer

Polyoxyethylene (10) polyoxypropylene (10) dimethyl ether (Compound 2)

$$CH_3O[(EO)_{10}/(PO)_{10}]CH_3 \qquad (III)$$

76 g of propylene glycol and 3.1 g of potassium hydroxide as a catalyst were placed in an autoclave. After the air in the autoclave was replaced with dry nitrogen, the catalyst was completely dissolved at 140° C. while stirring. Then, a mixture of 440 g of ethylene oxide and 522 g of propylene oxide was added dropwise thereto by a dripping apparatus and stirred for 2 hours. Thereafter, 224 g of potassium hydroxide was placed therein. After the atmosphere in the system was replaced with dry nitrogen, 188 g of methyl chloride was poured thereto under a pressure at a temperature of 80-130° C. to react for 5 hours. The reaction mixture was taken out from the autoclave, neutralized with hydrochloric acid to pH 6-7, and treated at 100° C. for 1 hour under a reduced pressure −0.095 MPa(50 mmHg) in order to remove the contained moisture. Further, in order to remove the salt produced after treatment, filtration was performed to obtain the alkylene oxide derivative of Formula (III).

A hydroxyl value of a sample which was taken out before reaction with methyl chloride and purified was 107, a hydroxyl value of the resulting compound of Formula (III) was 0.4, and a ratio of the number of terminal hydrogen atom with respect to the number of terminal methyl group was 0.004, thus, terminal hydrogen atoms were almost completely converted into methyl groups.

Synthesis Example 2

Synthesis of Block Polymer

Polyoxyethylene (10) polyoxypropylene (10) dimethyl ether (Compound 13)

$$CH_3O(EO)_5(PO)_{10}(EO)_5CH_3 \qquad (IV)$$

76 g of propylene glycol and 3.1 g of potassium hydroxide as a catalyst were placed in an autoclave. After the air in the autoclave was replaced with dry nitrogen, the catalyst was completely dissolved at 140° C. while stirring. 522 g of propylene oxide was added dropwise thereto by a dripping apparatus and stirred for 2 hours, and then 440 g of ethylene oxide was added dropwise thereto by a dripping apparatus and stirred for 2 hours. Then, 224 g of potassium hydroxide was placed therein. After the atmosphere in the system was replaced with dry nitrogen, 188 g of methyl chloride was poured thereto under a pressure at a temperature of 80-130° C. to react for 5 hours. The reaction mixture was taken out from the autoclave, neutralized with hydrochloric acid to pH 6-7, and treated at 100° C. for 1 hour under a reduced pressure −0.095 MPa(50 mmHg) in order to remove the contained moisture. Further, in order to remove the salt produced after treatment, filtration was performed to obtain the alkylene oxide derivative of Formula (IV).

A hydroxyl value of a sample which was taken out before reaction with methyl chloride and purified was 110, a hydroxyl value of the resulting compound of Formula (IV) was 0.3, and a ratio of the number of terminal hydrogen atom with respect to the number of terminal methyl group was 0.003, thus, terminal hydrogen atoms were almost completely converted into methyl groups.

I. Moisturizing and Rough Skin Improving Effects

The present inventors evaluated the conductance of each 10% aqueous solution of various humectants based on the aforementioned criteria.

TABLE 1

| Compound | Conductance | | |
|---|---|---|---|
| | 30 min-after | 60 min-after | 120 min-after |
| $CH_3O[(EO)_6/(PO)_{14}]CH_3$ | ◎ | ◎ | ◎ |
| $CH_3O[(EO)_{15}/(PO)_5]CH_3$ | ◎ | ◎ | ◎ |
| $CH_3O[(EO)_{25}/(PO)_{25}]CH_3$ | ◎ | ◎ | ◎ |
| Ion-exchange water | Δ | X | X |
| 1,3-Butylene glycol | Δ | Δ | Δ |
| Glycerin | ◎ | ○ | ○ |

As a result, it was revealed that the EO/PO derivative having hydrocarbon groups attached at both ends was excellent in the moisturizing property as compared with a general humectant such as 1,3-butylene glycol and glycerin. Therefore, the present inventors further studied the alkylene oxide derivative. First, using the tested basic composition A mentioned below evaluations as an external composition for skin were performed.

Tested basic composition A:

| | |
|---|---|
| Ethanol | 2 wt % |
| Glycerin | 5 |
| 1,3-Butylene glycol | 5 |
| Nicotinamide | 0.3 |
| Sodium pyrrolidonecarboxylate | 0.5 |
| Purified water | Balance |

(Determination of $R^1$ and $R^2$)

The correlation of $R^1$ and $R^2$ with the suitability as an external composition for skin was studied. The results are shown in the following Table 2. In Table 2, EO and PO of all compounds were $[(EO)_{10}/(PO)_{10}]$. Each compound was added to be 5% by weight with respect to the aforementioned basic composition A.

TABLE 2

| Comp. | $R^1$ | $R^2$ | Smoothness (1) | Stickiness (2) | Moisturizing Evol. No. (3) | Rough skin (4) | Stimulation A (5) |
|---|---|---|---|---|---|---|---|
| 1 | H | H | X | Δ | X | X | ○ |
| 2 | $CH_3$ | $CH_3$ | ◎ | ◎ | ◎ | ◎ | ◎ |
| 3 | $C_2H_5$ | $CH_3$ | ◎ | ◎ | ◎ | ◎ | ◎ |

TABLE 2-continued

| Comp. | $R^1$ | $R^2$ | Smoothness (1) | Stickiness (2) | Moisturizing Evol. No. (3) | Rough skin (4) | Stimulation A (5) |
|---|---|---|---|---|---|---|---|
| 4 | $C_4H_9$ | $C_4H_9$ | ○ | ○ | ○ | ○ | ○ |
| 5 | $C_6H_{13}$ | $CH_3$ | Δ | Δ | ○ | ○ | ○ |
| 6 | $C_{12}H_{25}$ | $CH_3$ | Δ | Δ | Δ | Δ | Δ |

As is clear from Table 2, when $R^1$ and $R^2$ had carbon numbers of 1-4 (Compound 2, 3, and 4), the excellent moisturizing effect and feeling of use could be obtained.

To the contrary, when $R^1$ and $R^2$ were hydrogen atoms (Compound 1), the sticky feeling was strong and, when $R^1$ was C12 (Compound 6), both of the moisturizing property and the feeling of use were not preferable. On the other hand, even in the case where a total of the carbon numbers of $R^1$ and $R^2$ was 7 and was less than that for Compound 4, when $R^1$ was C6 (Compound 5), there was a tendency that the moisturizing feeling is also deteriorated.

From the forgoing, it is necessary that both $R^1$ and $R^2$ are hydrocarbon groups having carbon numbers of 1-4 for a base of the present invention.

However, since upon practical preparation all of $R^1$ and $R^2$ are not necessarily replaced with a hydrocarbon group, we studied an acceptable existence ratio of the unsubstituted compound (i.e., $R^1$ or $R^2$=H). An unsubstituted ratio is expressed by Y/X which means a ratio of the number of a hydrogen atom (Y) with respect to the number of a hydrocarbon group (X). In the following Table 3, "1:2=5:95" means that Compound 1 and Compound 2 were mixed at a ratio of 5:95 to adjust it to the predetermined Y/X.

TABLE 3

| Comp. | $R^1$ | $R^2$ | Y/X | Stickiness (Evaluation 2) |
|---|---|---|---|---|
| 1 | H | H | — | Δ |
| 2 | $CH_3$ | $CH_3$ | 0.004 | ⊚ |
| 1:2 = 5:95 | | | 0.053 | ⊚ |
| 1:2 = 20:80 | | | 0.202 | Δ |

As is clear form the aforementioned Table 3, even if $R^1$ or $R^2$ is a hydrogen atom due to unreacting, when the ratio thereof is small (Y/X=0.053), there is no great influence. However, when Y/X becomes 0.202, the sticky feeling is clearly generated. The present inventors further studied the details and, as a result, it was made clear that Y/X of 0.15 or less is necessary.

(Oxyalkylene Group and Oxyethylene Group)

Then, a relationship between the presence of an oxyalkylene and an oxyethylene groups and the suitability as an external composition for skin was studied (Each compound was 5% by weight with respect to the aforementioned basic composition A).

The results are shown in Table 4. In Compounds 7-11, $R^1$ and $R^2$ are $CH_3$.

TABLE 4

| Comp. | EO | PO | (1) | (2) | Evaluation (3) | (4) | (5) |
|---|---|---|---|---|---|---|---|
| 7 | 20 | 0 | ○ | ○ | x | x | ○ |
| 8 | 15 | 5 | ⊚ | ⊚ | ⊚ | ⊚ | ⊚ |

TABLE 4-continued

| Comp. | EO | PO | (1) | (2) | Evaluation (3) | (4) | (5) |
|---|---|---|---|---|---|---|---|
| 2 | 10 | 10 | ⊚ | ⊚ | ⊚ | ⊚ | ⊚ |
| 9 | 6 | 14 | ⊚ | ⊚ | ⊚ | ⊚ | ⊚ |
| 10 | 0 | 20 | difficult to prepare(low water-soluble) | | | | |
| 11 | 25 | 25 | ⊚ | ○ | ⊚ | ⊚ | ⊚ |
| 12 | Formula(V)* | | ○ | Δ | x | x | Δ |

*Formula(V):

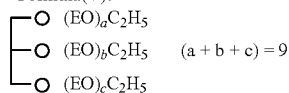

$(a + b + c) = 9$

As is clear from Table 4, the presence of both of an oxyalkylene group and an oxyethylene group is essential for the moisturizing property and the usability in the present invention. Also, since Compound 12 represented by Formula (V) has a low effect, it can be considered not to be simple effect of adjusting the hydrophilicity and the hydrophobicity. The detailed study by the present inventors revealed that a suitable ratio of the oxyethylene group with respect to a total of the oxyalkylene and oxyethylene groups is 20-80% by weight.

Further, the present inventors prepared and compared a block polymer and a random polymer having the same alkylene group number and oxyethylene group number

TABLE 5

| Compound | Stickiness (Evaluation 2) |
|---|---|
| 13 $CH_3O(EO)_5(PO)_{10}(EO)_5CH_3$ | ○ |
| 2 $CH_3O[(EO)_{10}/(PO)_{10}]CH_3$ | ⊚ |

As is clear from Table 5, although the effect of the present invention can be obtained in both block and random polymers, a random polymer is particularly excellent in the feeling of use.

(Amount in External Composition for Skin)

The amount of the alkylene oxide derivative of the present invention in an external composition for skin (the above-mentioned basic composition A) was further studied.

TABLE 6

| Evaluation No. | Compound 8 (%) | | | | | |
|---|---|---|---|---|---|---|
| | 0 | 0.01 | 0.5 | 5.0 | 40.0 | 70.0 |
| 1 | x | ○ | ⊚ | ⊚ | ⊚ | ⊚ |
| 2 | x | ○ | ⊚ | ⊚ | ⊚ | ○ |
| 3 | x | ○ | ⊚ | ⊚ | ⊚ | ⊚ |
| 4 | x | ○ | ⊚ | ⊚ | ⊚ | ⊚ |
| 5 | x | ○ | ⊚ | ⊚ | ⊚ | ⊚ |

From the results shown in Table 6, the effect of the compound of the present invention is perceived from around 0.01% by weight and, particularly remarkably, over 0.5% by weight. However, when it is 70% by weight, stickiness is initiated to be generated slightly and, therefore, it is preferable by around 40% by weight.

(Stickiness Improving Effect)

Further, regarding the alkylene oxide derivative of the present invention, during study on various incorporations, it was found that the alkylene oxide derivative had an effect of improving the stickiness due to a humectant such as glycerin. That is, in Table 6, also in a test composition containing no alkylene oxide derivative, the stickiness due to glycerin and the like is perceived. To the contrary, when the alkylene oxide derivative is added, it can not only suppress increase in the sticky feeling but also improve the stickiness due to humectants.

(Transdermal Absorption Promoting Effect)

As shown in the following Table 7, the alkylene oxide derivative (I) and glycerin themselves have the moisturizing effect and the rough skin improving effect, whereas these effects are remarkably improved synergistically in the composition where both are used.

TABLE 7

| Ingredient | Amount (%) | | |
|---|---|---|---|
| Alkylene oxide derivative* | 5 | — | 5 |
| Glycerin | — | 5 | 5 |
| Ion-exchange water | 95 | 95 | 90 |
| Evaluation in conductance measuring (120 min after) | Δ | Δ | ⊚ |

*$CH_3O[(EO)_{15}/(PO)_5]CH_3$

Then, the present inventors studied the action of the alkylene oxide derivative in more detail. As a result, it was also found that the alkylene oxide derivative in the present invention had the keratin permeation promoting activity of a general humectant such as glycerin. That is, as in FIG. 1, when the alkylene oxide derivative in the present invention is used together with glycerin (Sample 2), a permeation amount of glycerin was increased by about 40% as compared with the case of glycerin alone (control). A test method of FIG. 1 was as follows.

(I) Tested Sample

TABLE 8

| | Sample 1 (control) | Sample 2 |
|---|---|---|
| Glycerin | 10% | 10% |
| Alkylene oxide derivative* | 0 | 5 |
| Ion-exchange water | 90 | 85 |

*$CH_3O[(EO)_{15}/(PO)_5]CH_3$ (2) Test Method

The test was performed by a tape stripping method. The tape stripping method is a procedure in which a drug is applied and, thereafter, a keratin layer is peeled with a tape to determine the drug concentration in the keratin layer. This is a general method used as means to evaluate an amount of a drug absorbed into human skin. More specifically, an operation was performed in order of the following procedures (1)-(7) to examine the permeability of glycerin by an amount of glycerin recovered from a keratin layer peeled with a tape. The test was performed by 4 panelists and evaluated by an average thereof.

Procedure:
(1) A medial part of both forearms of panelists is washed with a soap.
(2) On a medial part of a forearm, a sample is applied (20 ml/20 cm²). In a right arm, Sample 1 is applied on a part near a wrist and Sample 2 is applied on a part near elbow joint. In a left arm, Samples 1 and 2 are applied on a reverse position as compared with a right arm.
(3) Allowing standing for 4 hours.
(4) The medial part of both forearms is washed with soap.
(5) A keratin layer is subjected to tape stripping (8 layers).
(6) Glycerin is extracted with ion-exchange water from tapes.
(7) Glycerin is quantitated (HPLC).

Further, the present inventors similarly studied using xylitol instead of glycerin as a humectant. A test method was the same as the aforementioned tape stripping method for glycerin except that allowing standing time in the procedure (3) was 6 hours. The samples used were as shown in the following Table 9.

TABLE 9

| | Sample 3 (control) | Sample 4 |
|---|---|---|
| Ethanol | 5 | 5 |
| Glycerin | 6 | 6 |
| Dipropylene glycol | 5 | 5 |
| Xylitol | 3 | 3 |
| Alkylene oxide derivative* | 0 | 5 |
| Ion-exchange water | 81 | 76 |

*$CH_3O[(EO)_{15}/(PO)_5]CH_3$

Figure 2:
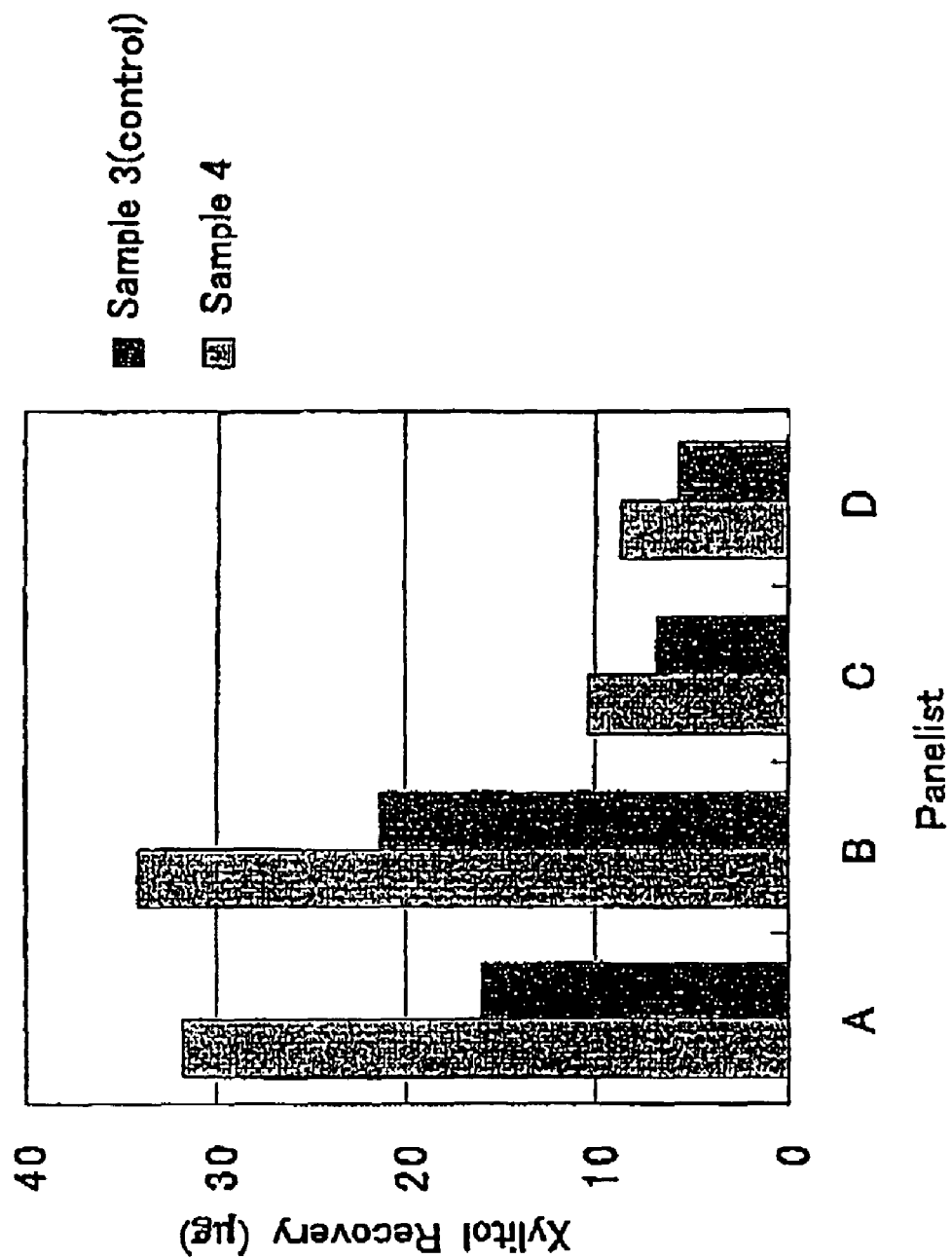
FIG. 2 shows a transdermal absorption promoting effect of an alkylene oxide derivative in accordance with the present invention to xylitol.

The results are shown in FIG. 2. As is clear from FIG. 2, in all cases of 4 panelists A-D, when the alkylene oxide derivative is incorporated (Sample 4), the amount of xylitol permeated into a keratin layer was increased as compared with Sample 3 containing no alkylene oxide derivative (control).

From the foregoing, it was suggested that alkylene oxide derivative (I) promotes the transdermal absorption of a humectant such as glycerin and xylitol.

Further, in order to investigate the effect of the alkylene oxide derivative on a hydrophilic medicament other than a humectant, the present inventors similarly studied using arbutin (hydroquinone-β-D-glucopyranoside). The test method was according to the aforementioned tape stripping method for glycerin. The samples used and the results thereof are shown in the following Table 10.

TABLE 10

| | Sample 5 (control) | Sample 6 |
|---|---|---|
| Glycerin | 10 | 10 |
| Alkylene oxide derivative* | 0 | 10 |
| Arbutin | 6 | 6 |
| Phenoxyethanol | 0.3 | 0.3 |
| Ethanol | 10 | 10 |
| Ion-exchange water | 73.7 | 63.7 |
| Arbutin Recovery (μg) | 0.9 | 4.6 |
| Glycerin Recovery (μg) | 129.7 | 156.8 |

*$CH_3O[(EO)_{15}/(PO)_5]CH_3$

As seen from Table 10, when the alkylene oxide derivative is incorporated (Sample 6), the amount of arbutin permeated into a keratin layer and that of glycerin were both increased as compared with Sample 5 containing no alkylene oxide derivative (control).

From the foregoing, it was suggested that the alkylene oxide derivative (I) promotes also the transdermal absorption of a skin whitening agent such as arbutin or the like.

Although the mechanism of the action on the transdermal absorption promoting effect of the alkylene oxide derivative of the present invention is not clear, it can be presumed that the alkylene oxide derivative promotes the transdermal absorption by decreasing the affinity of a hydrophilic medicament such as a humectant and a skin whitening agent with a base.

That is, theoretically, as the activity of a medicament in a base grows larger, the skin permeating rate of the medicament becomes larger. Therefore, in a region below the saturated solubility of a medicament, partition in skin can be increased by decreasing the affinity between a medicament and a base (i.e., by increasing a difference in values of solubility parameters of a medicament and a base).

A characteristic of the alkylene oxide derivative (I) of the present invention is not only the high water-solubility (the solubility in water is 100% or more) but also the high fat-solubility (the solubility in an ester oil is 100% or more). Such the solubility characteristic is derived from a chemical structure of the alkylene oxide derivative (I). There has been hardly such an aqueous base having both water-solubility and fat-solubility, and having the function which can greatly change a solubility parameter of a base by incorporation into an aqueous base and the excellent suitability as a base for an external composition for skin.

Therefore, it can be presumed that, by adding such the alkylene oxide derivative (I) to an aqueous base, a solubility parameter of the base is greatly changed and the affinity of a hydrophilic medicament such as a humectant with the base is remarkably decreased and, as a result, the keratin permeability is enhanced. Accordingly, when a medicament such as a humectant which is water-soluble and permeated into the skin to exert the effect, for example, a water-soluble vitamin and amino acid, a skin whitening agent or the like, is used as a hydrophilic medicament, improvement in the effect can be expected. Regarding a medicament which transdermal absorption promotion can be expected, a medicament having a high hydrophilicity is desirable. For example, although it is limited thereto, when a water/octanol partition coefficient (log P value) which expresses the water-solubility and the fat-solubility is used as one index, the coefficient of 0 or lower is effective and, more preferably −1 or low. Examples of a water-soluble medicament having the log P value of −1.0 or lower include hydroquinone glycosides and derivatives thereof, ascorbic acid and derivatives thereof, and salicylic acid derivatives. The log P value is a coefficient expressing the polarity by partition of a substance in water and octanol, which is defined, for example, in Chemical Reviews vol. 71(6), 525(1971).

On the other hand, it is considered that the alkylene oxide derivative can suppress the transdermal absorption of a fat-soluble medicament having the comparatively high keratin permeability conversely. For example, when a fat-soluble medicament is sobulilized or dispersed in an aqueous base, the alkylene oxide derivative shortens a difference in solubility parameters of the base and the medicament and enhances the affinity of the medicament and the base, thus, the keratin permeability is suppressed. Therefore, regarding a fat-soluble medicament which is desirably not permeated into skin (e.g., preservative and ultraviolet absorbing agent), a suppression of the transdermal absorption is expected by adding the alkylene oxide derivative. As for a medicament which transdermal absorption suppression can be expected, which is limited thereto, the water/octanol partition coefficient (log P value) of 0.5 or more is effective and, more preferably, 1.0 or more. Examples of a fat-soluble medicament having the log P value of 1.0 or more include methylparaben, ethylparaben, butylparaben, phenoxyethanol, octyl methoxysinnamate and the like.

From the foregoing, when the alkylene oxide derivative (I) of the present invention is added into an aqueous base, the transdermal absorption promoting activity can be exerted on a hydrophilic medicament such as a humectant and a skin-whitening agent. On the other hand, the transdermal absorption suppressing activity can be expected on a fat-soluble medicament such as a preservative and a ultraviolet absorbing agent. In addition, it can be presumed that in a lypophilic base the alkylene oxide derivative exerts the reverse action. Therefore, the alkylene oxide derivative of the present invention can function as a transdermal absorption controlling agent.

Since the nature of the alkylene oxide derivative (I) of the present invention can be adjusted by the number or a ratio of the EO and AO chains, it also has the advantage that the suitability for a subject medicament can be easily controlled.

In the following, preferable preparation examples in accordance with the present invention will be explained.

Preparation Example 1

Cream

| A. oil phase | |
|---|---|
| Stearic acid | 10.0 wt % |
| Stearyl alcohol | 4.0 |
| Stearyl butylate | 8.0 |
| Glyceryl monostearate | 2.0 |
| Vitamin E acetate | 0.5 |
| Vitamin A palmitate | 0.1 |
| Octyl methoxycinnamate | 2.0 |
| *Macademia* nut oil | 1.0 |
| Tea seed oil | 1.0 |
| Perfume | 0.4 |
| Antiseptic | Q.S. |
| B. water phase | |
| Compound 13 | 5.0 |
| Glycerin | 4.0 |
| 1,2-Pentanediol | 3.0 |
| Sodium hyaluronate | 1.0 |
| Potassium hydroxide | 2.0 |
| Magnesium ascorbate | 0.1 |
| L-Arginine hydrochloride | 0.01 |
| Trisodium edetate | 0.05 |
| Purified water | Balance |

(Preparation Method and Evaluation)

Each of the oil phase A and the water phase B was heated at 70° C. to dissolve perfectly. The phase A was added to the phase B and then the mixture was emulsified by an emufsifier. The emulsion was cooled by a heat exchanger to give a cream which had excellent smooth feeling and no-stickiness as well as moisturizing and rough skin improving effects.

Preparation Example 2

Cream

| A. oil phase | |
|---|---|
| Cetanol | 4.0 wt % |
| Vaseline | 7.0 |
| Isopropyl myristate | 8.0 |
| Squalane | 15.0 |
| Glyceryl monostearate | 2.2 |
| POE(20)sorbitane monostearate | 2.8 |
| Vitamin E nicotinate | 2.0 |
| Perfume | 0.3 |
| Antioxidant | Q.S. |
| Antiseptic | Q.S. |
| B. water phase | |
| Compound 2 | 10.0 |
| Glycerin | 10.0 |
| Sodium hyaluronate | 0.02 |
| Dipropylene glycol | 4.0 |
| Sodium pyrrolidonecarboxylate | 1.0 |
| Disodium edetate | 0.01 |
| Purified water | Balance |

(Preparation Method and Evaluation)

According to Preparation Example 1, a cream was prepared, which had excellent smooth feeling and no-stickiness as well as moisturizing and rough skin improving effects.

Preparation Example 3

Milky Lotion

| A. oil phase | |
|---|---|
| Squalane | 5.0 wt % |
| Oleyl oleate | 3.0 |
| Vaseline | 2.0 |
| Sorbitane sesquioleate | 0.8 |
| POE(20)oleyl ether | 1.2 |
| Evening primrose oil | 0.5 |
| Perfume | 0.3 |
| Antiseptic | Q.S. |
| B. water phase | |
| Compound 9 | 8.0 |
| 1,3-Butylene glycol | 4.5 |
| Ethanol | 3.0 |
| Carboxyvinyl polymer | 0.2 |
| Potassium hydroxide | 0.1 |
| L-Arginine L-aspartate | 0.01 |
| Edetate | 0.05 |
| Purified water | Balance |

(Preparation Method and Evaluation)

According to Preparation Example 1, a milky lotion was prepared, which had excellent smooth feeling and no-stickiness as well as moisturizing and rough skin improving effects.

Preparation Example 4

Foundation

| A. oil phase | |
|---|---|
| Cetanol | 3.5 wt % |
| Deodorized lanolin | 4.0 |
| Jojoba oil | 5.0 |
| Vaseline | 2.0 |
| Squalane | 6.0 |
| Glyceryl monostearate | 2.5 |
| POE(60)hydrogenated castor oil | 1.5 |
| POE(20)cetyl ether | 1.0 |
| Pyridoxine tripalmitate | 0.1 |
| Antiseptic | Q.S. |
| Perfume | 0.3 |
| B. water phase | |
| Compound 8 | 2.0 |
| Propylene glycol | 10.0 |
| Mixed powder | 12.0 |
| Trisodium ethylnediaminehydroxyethyltriacetate | 1.0 |
| Purified water | Balance |

(Preparation Method and Evaluation)

According to Preparation Example 1, a foundation was prepared, which had excellent smooth feeling and no-stickiness as well as moisturizing and rough skin improving effects.

Preparation Example 5

Lotion

| A. alcohol phase | |
|---|---|
| Ethanol | 5.0 wt % |
| POE oleyl ether | 2.0 |
| Compound 11 | 3.0 |
| Perfume | 0.05 |
| B. water phase | |
| 1,3-Butylene glycol | 9.5 |
| Sodium pyrrolidonecarboxylate | 0.5 |
| Nicotinamide | 0.3 |
| Glycerin | 5.0 |
| Dimorpholinopyridazinone | 0.1 |
| Purified water | Balance |

(Preparation Method and Evaluation)

The alcohol phase A was added solubilized into the water phase B to give a lotion which had excellent smooth feeling and no-stickiness as well as moisturizing and rough skin improving effects.

Preparation Example 6

Lipstick

| (1) Carnauba wax | 1.0 wt % |
|---|---|
| (2) Candelilla wax | 2.0 |
| (3) Ceresin | 10.0 |
| (4) Squalane | Balance |
| (5) Glyceryl triisooctanate | 9.0 |
| (6) Glyceryl diisostearate | 13.0 |
| (7) Compound 9 | 5.0 |
| (8) Silicone resin | 8.0 |
| (9) Hydroxypropyl-β-cyclodextrin | 1.0 |
| (10) *Macademia* nut oil fatty acid cholesteryl ester | 3.5 |
| (11) Synthetic magnesium sodium silicate | 0.5 |
| (12) Hydrophobic silica | 0.5 |
| (13) Purified water | 2.0 |
| (14) Boron nitride | 10.0 |
| (15) Coloring material | Q.S. |
| (16) Antiseptics | Q.S. |
| (17) Perfume | Q.S. |

(Preparation Method and Evaluation)

To (10) heated at 60° C., (11) and (12) were suspended. A uniform solution of (9) and (13) was added thereto and fully stirred. This mixture was added to a solution of (1)-(8) dissolved with heating and then fully stirred. (14)-(17) were further added thereto and suspended with stirring. Then, the suspension was poured into a case to give a lipstick, which had excellent smooth feeling and no-stickiness as well as moisturizing and rough skin improving effects.

Preparation Example 7

Milky Lotion

| | |
|---|---|
| POE(20) POP(2) cetyl ether | 1.0 wt % |
| Silicone KF96(20cs)(Shin-Etsu Chemical Co., Ltd.) | 2.0 |
| Liquid paraffin | 3.0 |
| Propylene glycol | 5.0 |
| Glycerin | 2.0 |
| Ethanol | 5.0 |
| Carboxyvinyl polymer | 0.3 |
| Hydroxypropylcellulose | 0.1 |
| 2-Aminomethylpropanol | 0.1 |
| Vitamin A acid | 0.05 |
| Alkylene oxide derivative | 2.0 |
| Hydroxyproline | 0.1 |
| Trehalose | 1.0 |
| Antiseptics | Q.S. |
| Perfume | Q.S. |
| Distilled water | Balance |

(Preparation Method and Evaluation)

According to a normal method, a milky lotion was prepared with the above ingredients. The resulting milky lotion had excellent smooth feeling and no-stickiness as well as moisturizing and rough skin improving effects.

Preparation Example 8

Astringency Lotion

| | |
|---|---|
| Dipropylene glycol | 2.0 wt % |
| Citric acid | 0.03 |
| Sodium citrate | 0.05 |
| Alkylene oxide derivative | 0.1 |
| Ethanol | 15.0 |
| POE(15) oleyl ether | 0.5 |
| Hydroxyproline | 0.03 |
| Trehalose | 0.5 |
| Antiseptics | Q.S. |
| Perfume | Q.S. |
| Distilled water | Balance |

(Preparation Method and Evaluation)

According to a normal method, a lotion was prepared with the above ingredients. The resulting lotion had excellent smooth feeling and no-stickiness as well as moisturizing and rough skin improving effects.

Preparation Example 9

Cream

| | |
|---|---|
| A. oil phase | |
| Cetanol | 2.0 wt % |
| Vaseline | 2.0 |
| Squalane | 20.0 |
| Glyceryl mono-fatty acid ester | 2.0 |
| Tween 60 (POE(20) sorbitan monostearate) | 3.0 |
| Isopropyl myristate | 6.0 |
| Stearyl glycyrrhetinate | 0.5 |
| Glyceryl mono-2-ethylhexanoyl-diparamethoxycinnamate | 0.05 |
| 4-Methoxy-4'-t-butyldibenzoylmethane | 0.05 |
| BHT | 0.01 |
| Antiseptics | 0.3 |
| Perfume | 0.2 |
| B. water phase | |
| Glycerin | 10.0 |
| Propylene glycol | 5.0 |
| Alkylene oxide derivative | 0.1 |
| Hydroxyproline | 0.05 |
| Trehalose | 5.0 |
| Trisodium edetate | 0.1 |
| Potassium hydroxide | 1.0 |
| Distilled water | Balance |

(Preparation Method and Evaluation)

Each of the oil phase A and the water phase B was heated with 70° C. and dissolved perfectly. The oil phase A was mixed in the water phase B and emulsified by a emulsifier. The emulsion was cooled by a heat exchanger to a final temperature at 30° C. to give a cream which had excellent smooth feeling and no-stickiness as well as moisturizing and rough skin improving effects.

As explained in the above, by incorporating an alkylene oxide derivative, an external composition for skin of the present invention is excellent in the feeling of use, particularly, in the smooth feeling and no stickiness, and has the moisturizing and rough skin improving effects. In addition, when a general humectant other than the alkylene oxide derivative is used together therewith, the derivative promotes the keratin permeability of the humectant, and the moisturizing and rough skin improving effects are remarkably improved. Further, it promotes the transdermal absorption also on a skin-whitening agent.

II. Refreshing Effect

The influence of the alkylene oxide derivative of the present invention on the refreshing effect and stimulation of a refreshing agent was studied. An external composition for skin was prepared according to the following tested basic composition B and evaluated.

Tested basic composition B:

| | |
|---|---|
| (1) Ethanol | 5.0 wt % |
| (2) Glycerin | 3.0 |
| (3) 1,3-Butylene glycol | 5.0 |
| (4) L-Menthol | 0.1 |
| (5) Tested compound | 5.0 |
| (6) Purified water | Balance |

TABLE 11

| | Evaluation | |
|---|---|---|
| Tested compound | Stimulation B (7) | Refreshing feeling durability (8) |
| $CH_3O[(EO)_6/(PO)_{14}]CH_3$ | ◎ | ◎ |
| $CH_3O[(EO)_{16}/(PO)_5]CH_3$ | ◎ | ◎ |
| $CH_3O[(EO)_{25}/(PO)_{25}]CH_3$ | ◎ | ◎ |
| Glycerin | Δ | X |
| Ion-exchange water | X | X |

As seen from Table 11, when a general humectant such as glycerin is used, the skin stimulation (smart feeling) due to the refreshing agent is improved a little, but the refreshing feeling durability can not be enhanced. In addition, the stickiness due to the humectant may be generated.

On the other hand, when the EO/PO derivative having hydrocarbon groups attached at both ends is used, a mild refreshing feeling lasted for a long time and there were no skin stimulation (no smart feeling) and no stickiness.

Figure 3:
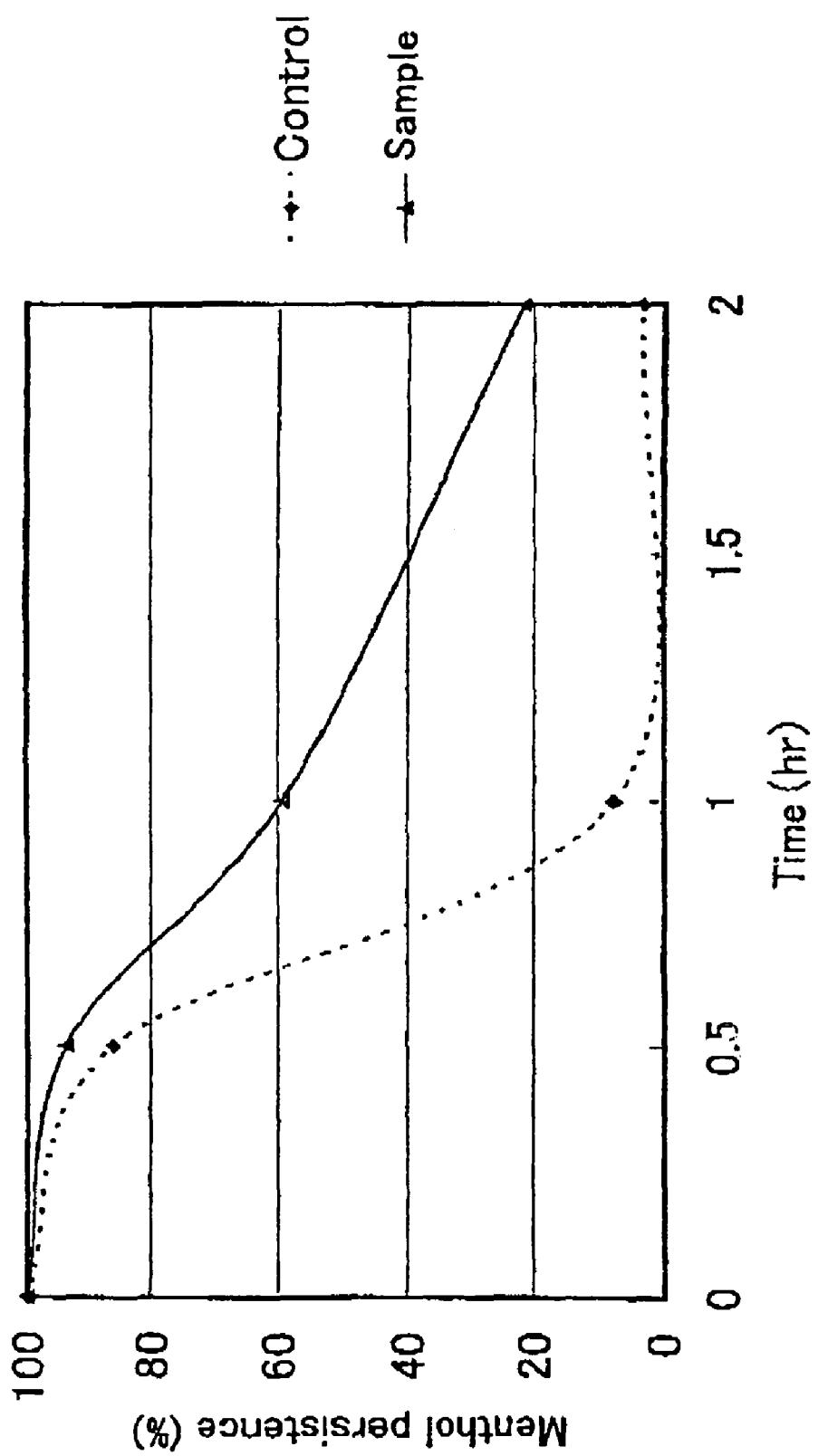
FIG. 3 shows a change in release of menthol together with or without an alkylene oxide derivative in accordance with the present invention.

Then, a change of releasing property of menthol from a composition with or without the alkylene oxide derivative was studied. The result is shown in FIG. 3, wherein the control is an ethanol solution, whereas the sample is 10% alkylene oxide derivative solution in ethanol. In both solutions, first concentration of menthol was 1%. As for the alkylene oxide derivative, a compound of $CH_3O[(EO)_{15}/(PO)_5]CH_3$ was used. A sampling was conducted temporally from each solution while being placed in open system at room temperature and the concentration of menthol was measured to calculate its persistence therefrom.

As seen from FIG. 3, when no alkylene oxide derivative is used, menthol is almost released at one stroke for first 1 hour. Therefore, the effect of menthol can not last and a smart feeling is easily generated. On the other hand, when the alkylene oxide derivative is used, it can be considered that menthol is released gradually and the effect can last for a long time to give a mild refreshing feeling for a long time without a smart feeling.

Figure 4:
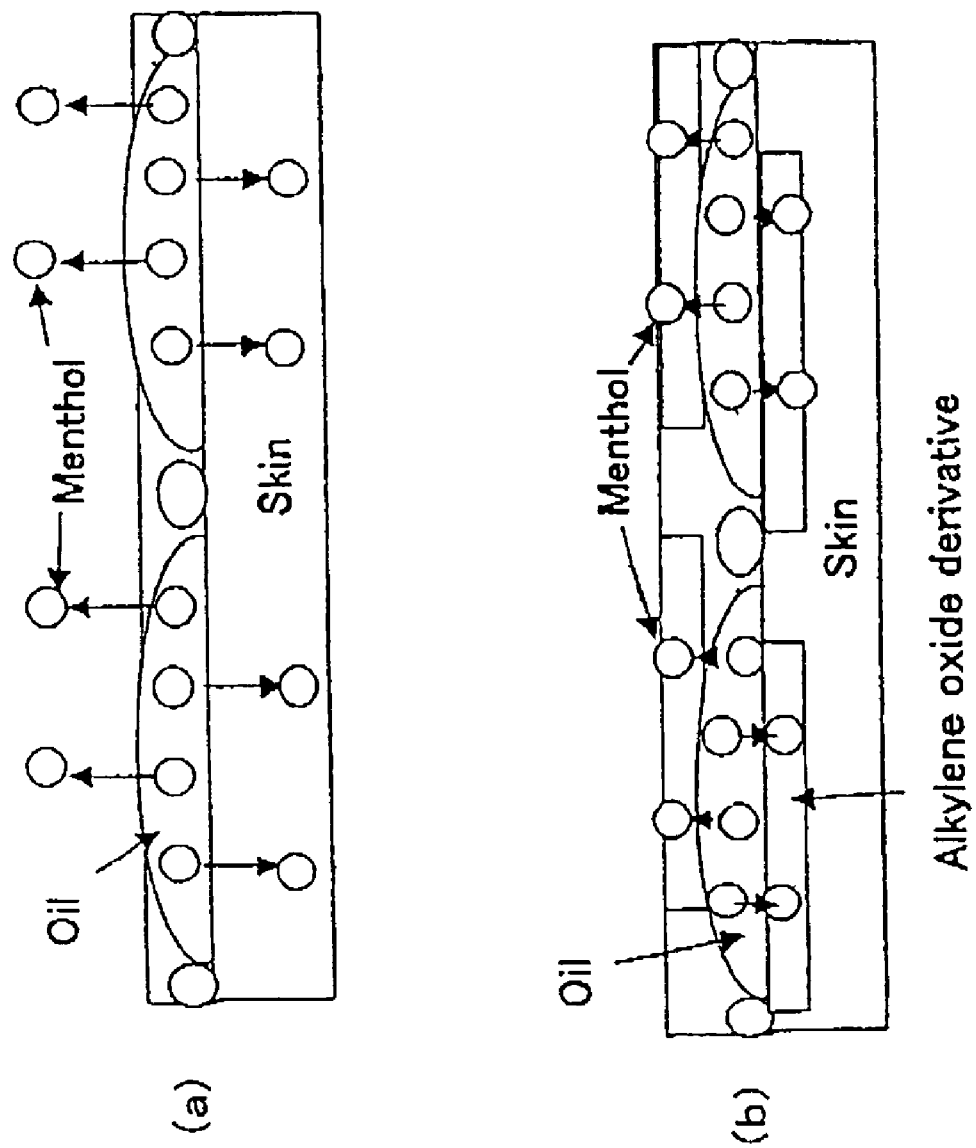
FIG. 4 shows a model for release of menthol from: (a) a composition including no alkylene oxide derivative in accordance with the present invention; and (b) a composition including an alkylene oxide derivative in accordance with the present invention.

Although the mechanism of action of the alkylene oxide derivative on a refreshing agent is not clear, it can be considered as follows. FIG. 4 shows an example of a model for an o/w emulsion containing menthol. In the case (a) which is a composition containing no alkylene oxide derivative, menthol is released vigorously. On the other hand, in the case (b) which is a composition containing the alkylene oxide derivative, it can be considered that the alkylene oxide derivative holds menthol in the base due to its good compatibility with both water and menthol and, as a result, menthol is released gradually to give a mild refreshing effect lasting for a long time and to lower the stimulation such as a smart feeling.

Further, the study for alkylene oxide derivative was proceeded. For each test, a composition prepared according to the above-mentioned basic composition B was used.

(Determination of $R^1$ and $R^2$)

The correlation of $R^1$ and $R^2$ of the present invention with the suitability as an external composition for skin was studied. The results are shown in the following Table 12, wherein EO and PO of all compounds were $[(EO)_{10}/(PO)_{10}]$.

As is clear from Table 12, when $R^1$ and $R^2$ had carbon numbers of 1-4 (Compound 2, 3, and 4), the refreshing feeling remaining effect and favorable feeling of use could be obtained and there was hardly skin stimulation such as a smart feeling.

To the contrary, when $R^1$ and $R^2$ were hydrogen atoms (Compound 1) and when $R^1$ was C12 (Compound 6), the results in all evaluations become to be unfavorable. On the other hand, even in the case where a total of the carbon numbers of $R^1$ and $R^2$ was 7 and was less than that for Compound 4, when $R^1$ was C6 (Compound 5), there was a tendency that the feeling of use was also deteriorated.

From the forgoing, it is necessary that both $R^1$ and $R^2$ are hydrocarbon groups having carbon numbers of 1-4 for the alkylene oxide derivative of the present invention.

However, since upon practical preparation, all of $R^1$ and $R^2$ are not necessarily replaced with a hydrocarbon group, we studied an acceptable existence ratio of the unsubstituted compound (i.e., $R^1$ or $R^2$=H). An unsubstituted ratio is expressed by Y/X which means a ratio of the number of a hydrogen atom (Y) with respect to the number of a hydrocarbon group (X). In the following Table 13, "1:2=5:95" means that Compound 1 and Compound 2 were mixed at a ratio of 5:95 to adjust it to the predetermined Y/X.

TABLE 13

| Comp. No. | $R^1$ | $R^2$ | Y/X | Compatibility (6) | Smoothness (1) | Stickiness (2) | Stimulation B (7) | Refreshing feeling (8) |
|---|---|---|---|---|---|---|---|---|
| 1 | H | H | — | X | X | Δ | Δ | X |
| 2 | CH₃ | CH₃ | 0.004 | ⊚ | ⊚ | ⊚ | ⊚ | ⊚ |
| 1:2 = 5:95 | | | 0.053 | ⊚ | ⊚ | ⊚ | ⊚ | ⊚ |
| 1:2 = 20:80 | | | 0.202 | ○ | Δ | Δ | Δ | ○ |

As is clear form the aforementioned Table 13, even if $R^1$ or $R^2$ is a hydrogen atom due to unreacting, when the ratio thereof is small (Y/X=0.053), there is no great influence. However, when Y/X becomes 0.202, each effect is clearly lowered. The present inventors further studied the details and, as a result, it was made clear that Y/X of 0.15 or less is necessary.

(Oxyalkylene Group and Oxyethylene Group)

Then, a relationship between the presence of an oxyalkylene and an oxyethylene groups in the alkylene oxide derivative and the suitability as an external composition for skin was studied The results are shown in Table 14. In Compounds 2 and 7-11, $R^1$ and $R^2$ are $CH_3$.

TABLE 12

| Tested Comp. | $R^1$ | $R^2$ | Compatibility (6) | Smoothness (1) | Stickiness (2) | Stimulation B (7) | Refreshing feeling (8) |
|---|---|---|---|---|---|---|---|
| 1 | H | H | X | X | Δ | Δ | X |
| 2 | CH₃ | CH₃ | ⊚ | ⊚ | ⊚ | ⊚ | ⊚ |
| 3 | C₂H₅ | CH₃ | ⊚ | ⊚ | ⊚ | ⊚ | ⊚ |
| 4 | C₄H₉ | C₄H₉ | ○ | ○ | ○ | ○ | ○ |
| 5 | C₆H₁₃ | CH₃ | Δ | Δ | Δ | ○ | ○ |
| 6 | C₁₂H₂₅ | CH₃ | Δ | Δ | Δ | Δ | Δ |

TABLE 14

| Comp. No. | EO | PO | Compatibility (6) | Smoothness (1) | Stickiness (2) | Stimulation B (7) | Refreshing feeling (8) |
|---|---|---|---|---|---|---|---|
| 7 | 20 | 0 | ○ | ○ | ○ | Δ | Δ |
| 8 | 15 | 5 | ⊙ | ⊙ | ⊙ | ⊙ | ⊙ |
| 2 | 10 | 10 | ⊙ | ⊙ | ⊙ | ⊙ | ⊙ |
| 9 | 6 | 14 | ⊙ | ⊙ | ⊙ | ⊙ | ⊙ |
| 10 | 0 | 20 | difficult to prepare(low water-soluble) | | | | |
| 11 | 25 | 25 | ⊙ | ⊙ | ○ | ⊙ | ⊙ |
| 12 | Formula (V)* | | Δ | ○ | Δ | Δ | x |

*Formula (V):

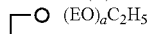
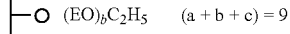  (a + b + c) = 9
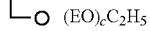

As is clear from Table 14, the presence of both of an oxyalkylene group and an oxyethylene group is essential for the effect of the present invention. Also, since Compound 12 represented by Formula (V) has a low effect, it can be considered not to be simple effect of adjusting the hydrophilicity and the hydrophobicity. The detailed study by the present inventors revealed that a suitable ratio of the oxyethylene group with respect to a total of the oxyalkylene group and the oxyethylene group is 20-80% by weight.

Further, the present inventors compared a block polymer and a random polymer having the same alkylene group number and oxyethylene group number.

TABLE 15

| Compound | Stickiness (Evaluation 2) |
|---|---|
| 13 $CH_3O(EO)_5(PO)_{10}(EO)_5CH_3$ | ○ |
| 2 $CH_3O[(EO)_{10}/(PO)_{10}]CH_3$ | ⊙ |

As is clear from Table 15, although the effect of the present invention can be obtained in both block and random polymers, a random polymer is particularly excellent in the feeling of use.

(Amount in External Composition for Skin)

The amount of the alkylene oxide derivative of the present invention in an external composition for skin was further studied. Namely, by using Compound 8 in the above-mentioned basic composition B, an external composition for skin was prepared, wherein total amount was adjusted with purified water. The result in each evaluation is shown in Table 16.

TABLE 16

| Compound 8 (%) | Compatibility (6) | Smoothness (1) | Stickiness (2) | Stimulation B (7) | Refreshing feeling (8) |
|---|---|---|---|---|---|
| 0 | X | X | X | X | X |
| 0.1 | ○ | ○ | ○ | ○ | ○ |
| 5.0 | ⊙ | ⊙ | ⊙ | ⊙ | ⊙ |
| 40.0 | ⊙ | ⊙ | ⊙ | ⊙ | ⊙ |
| 80.0 | ⊙ | ⊙ | ○ | ⊙ | ⊙ |

From the results shown in Table 16, the effect of the alkylene oxide derivative of the present invention is perceived from around 0.01% by weight and, particularly remarkably, over 0.5% by weight. However, when it is 80% by weight, stickiness is initiated to be generated slightly and, therefore, it is preferable by around 40% by weight.

In the following, preferable preparation examples containing a refreshing agent in accordance with the present invention will be explained.

Preparation Example 1

Lotion

| A. alcohol phase | |
|---|---|
| Ethanol | 5.0 wt % |
| POE oleyl ether | 2.0 |
| Compound 6 | 3.0 |
| 2-Ethylhexyl p-dimethylaminobenzoate | 0.18 |
| l-Menthol | 0.01 |
| Perfume | 0.05 |
| B. water phase | |
| 1,3-Butylene glycol | 9.5 |
| Sodium pyrrolidonecarboxylate | 0.5 |
| Nicotinamide | 0.3 |
| Glycerin | 5.0 |
| Purified water | to 100 |

(Preparation Method and Evaluation)

The alcohol phase A was added and solubilized into the water phase B to give a lotion, which was excellent in the durability of refreshing feeling and had a favorable feeling of use without stimulation.

Preparation Example 2

Milky Lotion (O/W)

| A. oil phase | |
| --- | --- |
| Stearic acid | 3.0 wt % |
| Cetanol | 1.0 |
| Lanolin derivatives | 3.0 |
| Liquid paraffin | 5.0 |
| 2-Ethylhexyl stearate | 3.0 |
| l-Menthol | 0.3 |
| d-Camphor | 0.1 |
| POE cetyl ether | 2.0 |
| Glyceryl monostearate | 2.0 |
| Antiseptic | Q.S. |
| Perfume | Q.S. |
| B. water phase | |
| 1,3-Butylene glycol | 6.0 |
| Triethanolamine | 1.0 |
| Compound 2 | 20.0 |
| Purified water | to 100 |

(Preparation Method and Evaluation)

The water phase B was mixed and dissolved to be maintained at 70° C. After the oils of the oil phase A was heated and dissolved at 70-80° C., the other ingredients were added thereto and kept at 70° C. To the water phase the oil phase was added and emulsified while being stirred to give a milky lotion, which was excellent in the durability of refreshing feeling and had a favorable feeling of use without stimulation.

Preparation Example 3

Calamine Lotion

| A. ethanol phase | |
| --- | --- |
| Ethanol | 15 wt % |
| Glycerin | 2 |
| 1,3-Butylene glycol | 2 |
| Compound 13 | 10 |
| Perfume | Q.S. |
| B. powder phase | |
| Iron oxide red | 0.15 |
| Zinc oxide | 0.5 |
| Kaolin | 2.0 |
| C. water phase | |
| Camphor | 0.2 |
| Phenol | 0.02 |
| Purified water | to 100 |

(Preparation Method and Evaluation)

The ethanol phase A was mixed and dissolved. To the water phase mixed and dissolved, the powder phase and the ethanol phase were added and stirred to suspend powders, thereby giving a calamine lotion, which was excellent in the durability of refreshing feeling and had a favorable feeling of use without stimulation.

Preparation Example 4

Cream (O/W)

| A. oil phase | |
| --- | --- |
| Stearyl alcohol | 6.0 wt % |
| Stearic acid | 2.0 |
| Hydrogenated lanolin | 4.0 |
| Squalane | 9.0 |
| Octyldodecanol | 10.0 |
| l-Menthol | 0.3 |
| d-Camphor | 0.1 |
| POE cetyl ether | 3.0 |
| Glyceryl monostearate | 2.0 |
| Antiseptic | Q.S. |
| Perfume | Q.S. |
| B. water phase | |
| 1,3-Butylene glycol | 6.0 |
| PEG 1500 | 4.0 |
| Compound 2 | 20.0 |
| Purified water | to 100 |

(Preparation Method and Evaluation)

The water phase B was mixed, dissolved and kept at 70° C. After the oils of the oil phase A was heated and dissolved at 70-80° C., the other ingredients were added thereto and kept at 70° C. To the water phase the oil phase was added while being stirred and emulsified by a homomixer uniformly and the emulsion was deaerated, filtrated and cooled to give a cream, which was excellent in the durability of refreshing feeling and had a favorable feeling of use without stimulation.

Preparation Example 5

Gel (Aqueous Moisturizing Gel)

| A. moisturizing agent phase | |
| --- | --- |
| Dipropylene glycol | 7.0 wt % |
| POE oleyl ether | 2.0 |
| l-Menthol | 0.01 |
| Perfume | 0.05 |
| Antiseptic | Q.S. |
| B. water phase | |
| Carboxyvinyl polymer | 0.4 |
| Methylcellulose | 0.2 |
| PEG 1500 | 8.0 |
| Compound 2 | 3.0 |
| Potassium hydroxide | 0.1 |
| Anti-browning agent | Q.S. |
| Chelating agent | Q.S. |
| Coloring material | Q.S. |
| Purified water | to 100 |

(Preparation Method and Evaluation)

After the water-soluble polymer was dissolved in purified water uniformly, PEG1500, Compound 2, anti-browning agent, coloring material and chelating agent were added thereto to prepare the water phase B. To dipropylene glycol the surfactant was added and the mixture was heated and dissolved at 50-55° C., and then antiseptic, perfume and menthol were further added thereto to prepare the moisturizing agent phase A. To the phase A, the water phase B was added gradually while being stirred. Finally, the aqueous basic solution was added thereto and fully stirred for notarization. The resulting gel was excellent in the durability of refreshing feeling and had a favorable feeling of use without stimulation.

Preparation Example 6

Deodorant Stick (Wax Type Stick)

| | | |
|---|---|---|
| Aluminum chlorohydrate | 23.0 | wt % |
| Talc | 15.0 | |
| Solid paraffin wax | 2.0 | |
| Stearyl alcohol | 8.0 | |
| Liquid paraffin | 14.5 | |
| Cyclic dimethylpolysiloxane | 26.5 | |
| Sorbitane fatty acid ester | 1.0 | |
| Compound 6 | 10.0 | |
| l-Menthol | 0.01 | |
| Perfume | Q.S. | |

(Preparation Method and Evaluation)

Solid paraffin wax, stearyl alcohol and sorbitane fatty acid ester were heated and dissolved to liquid paraffin to be mixed. Powders, Compound 6, 1-menthol, cyclic dimethylpolysiloxane and perfume were further added thereto and the mixture was mixed and suspended by a homomixer uniformly and then pored into a case to be cooled and solidified. The resulting wax stick was excellent in the durability of refreshing feeling and had a favorable feeling of use without stimulation.

Preparation Example 7

Hair Tonic

| | | |
|---|---|---|
| Extract of *Sophora flavescens* A.(Chinese name: Kujin) (50% ethanol extract) | 1.0 | wt % (dry weight: 0.04) |
| N,N-Bis(2-hydroxyethyl)-tetracosylamine oxide | 1.0 | |
| N,N-Dimethyldecylamine oxide | 1.0 | |
| Compound 13 | 5.0 | |
| Hinokitiol | 1.0 | |
| Vitamin $B_6$ | 0.2 | |
| Vitamin E acetate | 0.02 | |
| Menthol | 0.2 | |
| Swertia herb extract | 1.0 | |
| Salicylic acid | 0.1 | |
| Extract of *Rosa rugosa* Thunb.(Chinese name: Maikaika) (ethanol extract) | 0.5 | |
| Propylene glycol | 2.0 | |
| Sodium hyaluronate | 0.01 | |
| Polyoxyethylene(10)monostearate | 2.0 | |
| 75% Ethanol | Balance | |

(Preparation Method and Evaluation)

According to a normal method, a hair tonic was prepared with the above ingredients. The resulting hair tonic was excellent in the durability of refreshing feeling and had a favorable feeling of use without stimulation.

In the foregoing, by using a refreshing agent and a special alkylene oxide derivative, the present invention can provide an external composition for skin lasting a refreshing effect for a long time and having favorable feeling of use without stimulation such as a smart feeling.

We claim:

1. A cosmetic method for skin or hair, comprising:
applying externally to said skin or hair a composition comprising an alkylene oxide derivative expressed by Formula (I):

$$R^1O\text{-}[(AO)_m(EO)_n]\text{-}R^2 \qquad (I)$$

wherein AO is an oxyalkylene group having a carbon number of 3 or 4; EO is an oxyethylene group; m and n are average addition numbers of said AO and EO, respectively, which are $1 \leq m \leq 70$ and $1 \leq n \leq 70$,
wherein said EO is 20-80% by weight with respect to a total of said AO and EO;
wherein said AO and EO are added to each other in block or random form;
wherein $R^1$ and $R^2$ are either identical to or different from each other, and
wherein said $R^1$ and said $R^2$ are alkyl groups having a carbon number of 1-4.

2. The method of claim 1, wherein said alkylene oxide derivative is 0.01-80% by weight of said composition.

3. The method of claim 1, wherein said composition further comprises a water-soluble medicament.

4. The method of claim 1, wherein said composition further comprises a humectant.

5. The method of claim 4, wherein said humectant is xylitol or glycerin.

6. The method of claim 1, wherein said composition further comprises a skin whitening agent.

7. The method of claim 6, wherein said skin whitening agent is selected from the group consisting of arbutin, ascorbyl glucoside, magnesium ascorbyl phosphate and ethyl ascorbic acid.

8. The method of claim 1, wherein said composition further comprises a refreshing agent.

9. The method of claim 8, wherein said refreshing agent is menthol or camphor.

10. The method of claim 1, wherein said $R^1$ is methyl or ethyl and said $R^2$ is methyl.

11. The method of claim 1, wherein said AO and EO are added to each other in random form.

12. The method of claim 1, wherein said alkylene oxide is a moisturizing agent, a rough skin or hair improving agent, a stickiness improving agent, or a transdermal absorption improving agent.

13. A method for improving transdermal absorption of a water-soluble medicament comprising:
adding to an external composition containing the water-soluble medicament an effective amount of an alkylene oxide derivative expressed by Formula (I):

$$R^1O\text{-}[(AO)_m(EO)_n]\text{-}R^2 \qquad (I)$$

wherein AO is an oxyalkylene group having a carbon number of 3 or 4; EO is an oxyethylene group; m and n are average addition numbers of said AO and EO, respectively, which are $1 \leq m \leq 70$ and $1 \leq n. \leq 70$,
wherein said EO is 20%-80% by weight with respect to a total of said AO and EO;
wherein said AO and EO are added to each other in block or random form;
wherein $R^1$ and $R^2$ are either identical to or different from each other, and
wherein said $R^1$ and said $R^2$ are alkyl groups having a carbon number of 1-4.

14. The method of claim 13, wherein said external composition is a cream, a lotion, a foundation, a lipstick, a gel, a deodorant stick, or a hair tonic.

15. The method of claim 13, wherein said $R^1$ is methyl or ethyl and said $R^2$ is methyl.

16. The method of claim 13, wherein said AO and DO are added to each other in random form.

17. The method of claim 13, wherein said water-soluble medicament is a humectant.

18. The method of claim 17, wherein said humectant is xylitol or glycerin.

19. The method of claim 13, wherein said water-soluble medicament is a skin whitening agent.

20. The method of claim 19, wherein said skin whitening agent is selected from the group consisting of arbutin, ascorbyl glucoside, magnesium ascorbyl phosphate and ethyl ascorbic acid.

21. A method for improving a stickiness of an external composition for skin or hair, comprising:

adding to said external composition an effective amount of an alkylene oxide derivative expressed by Formula (I):

$$R^1O\text{-}[(AO)_m(EO)_n]\text{---}R^2 \qquad (I)$$

wherein AO is an oxyalkylene group having a carbon number of 3 or 4; EO is an oxyethylene group; m and n are average addition numbers of said AO and EO, respectively, which are $1 \leq m \leq 70$ and $1 \leq n. \leq 70$, wherein said EU is 20-80% by weight with respect to a total of said AO and EO;

wherein said AO and O are added to each other in block or random form;

wherein $R^1$ and $R^2$ are either identical to or different from each other, and wherein said $R^1$ and said $R^2$ are alkyl groups having a carbon number of 1-4.

22. The method of claim 21, wherein said external composition further comprises a humectant.

23. The method of claim 21, wherein said $R^1$ is methyl or ethyl and said $R^2$ is methyl.

24. The method of claim 21, wherein said AO and EO are added to each other in random form.

25. A method for moisturizing human skin comprising: applying an external composition on human skin or hair, the external composition comprising: an alkylene oxide derivative expressed by Formula (I):

$$R^1O\text{-}[(AO)_m(EO)_n]\text{---}R^2 \qquad (I)$$

wherein AO is an oxyalkylene group having a carbon number of 3 or 4; EO is an oxyethylene group; m and n are average addition numbers of said AO and EO, respectively, which are $1 \leq m \leq 70$ and $1 \leq n \leq 70$, wherein said EO is 20-80% by weight with respect to a total of said AO and EO;

wherein said AO and BO are added to each other in block or random form;

wherein $R^1$ and $R^2$ are either identical to or different from each other, and wherein said $R^1$ and said $R^2$ are alkyl groups having a carbon number of 1-4.

26. The method of claim 25, wherein said $R^1$ is methyl or ethyl and said $R^2$ is methyl.

27. The method of claim 25, wherein said AO and BO are added to each other in random form.

28. A method for improving human rough skin or hair, comprising applying an external composition on human skin or hair, the external composition comprising: an alkylene oxide derivative expressed by Formula (I):

$$R^1O\text{-}[(AO)_m(EO)_n]\text{---}R^2 \qquad (I)$$

wherein AO is an oxyalkylene group having a carbon number of 3 or 4; EO is an oxyethylene group; m and n are average addition numbers of said AO and EO, respectively, which are $1 \leq m \leq 70$ and $1 \leq n \leq 70$, wherein said EO is 20-80% by weight with respect to a total of said AO and EO;

wherein said AO and EO are added to each other in block or random form;

wherein $R^1$ and $R^2$ are either identical to or different from each other, and wherein said $R^1$ and said $R^2$ are alkyl groups having a carbon number of 1-4.

29. The method of claim 28, wherein said $R^1$ is methyl or ethyl and said $R^2$ is methyl.

30. The method of claim 28, wherein said AO and EO are added to each other in random form.

* * * * *